(12) United States Patent
Uesugi et al.

(10) Patent No.: US 8,685,976 B2
(45) Date of Patent: Apr. 1, 2014

(54) CELL ADHESION PROMOTING AGENT AND METHOD OF PROMOTING CELL ADHESION

(75) Inventors: Motonari Uesugi, Uji (JP); Sayumi Yamazoe, Uji (JP)

(73) Assignee: Kyoto University, Kyoto (JP)

( * ) Notice: Subject to any disclaimer, the term of this patent is extended or adjusted under 35 U.S.C. 154(b) by 330 days.

(21) Appl. No.: 12/999,805

(22) PCT Filed: Jun. 16, 2009

(86) PCT No.: PCT/JP2009/060950
§ 371 (c)(1),
(2), (4) Date: Feb. 2, 2011

(87) PCT Pub. No.: WO2009/154201
PCT Pub. Date: Dec. 23, 2009

(65) Prior Publication Data
US 2011/0117651 A1    May 19, 2011

(30) Foreign Application Priority Data

Jun. 18, 2008  (JP) ................................ 2008-159369

(51) Int. Cl.
*A01N 43/66*  (2006.01)
*A61K 31/53*  (2006.01)
*A61K 31/497* (2006.01)
*C07D 403/00* (2006.01)

(52) U.S. Cl.
USPC ...... 514/245; 514/252.13; 544/212; 544/296; 544/359

(58) Field of Classification Search
USPC ........ 514/252.11, 245, 252.13; 544/357, 212, 544/296, 359
See application file for complete search history.

(56) References Cited

U.S. PATENT DOCUMENTS 4,481,201 A   11/1984   Dorokhova et al.

FOREIGN PATENT DOCUMENTS

| DE | 31 43 592    | 5/1983 |
| DE | 249 382      | 9/1987 |
| DE | 198 51 375   | 5/2000 |
| DE | 103 50 929 A1 | 6/2005 |

OTHER PUBLICATIONS

Cheshenko et. al., Molecular Biology of the Cell, 2007, The American Society for Cell Biology, vol. 18, pp. 3119-3130.*
International Search Report issued Sep. 15, 2009 in International (PCT) Application No. PCT/JP2009/060950.
A.G. Artemenko et al., "Identification of Individual Structural Fragments of N,N'-(bis-5-nitropyrimidyl) dispirotripiperazine Derivatives for Cytotoxicity and Antiherpetic Activity Allows the Prediction of New Highly Active Compounds," J. Antimicrobial Chemotherapy, vol. 60, pp. 68-77, 2007.
M. Schmidtke et al., "Synthesis, Cytotoxicity and Antiviral Activity of N,N'-bis-5-nitropyrimidyl Derivatives of Dispirotripiperazine," Antiviral Res., vol. 55, pp. 117-127, 2002.
M. Schmidtke et al., "Binding of N,N'-bisheteryl Derivative of Dispirotripiperazine to Heparan Sulfate Residues on the Cell Surface Specifically Prevents Infection of Viruses from Different Families," Virology, vol. 311, pp. 134-143, 2003.
Lian-Sheng Li et al., "Chemical Adaptor Immunotherapy: Design, Synthesis, and Evaluation of Novel Integrin-Targeting Devices," J. Med. Chem., vol. 47, pp. 5630-5640, 2004.
Sayumi Yamazoe et al., "A Dumbbell-Shaped Small Molecule that Promotes Cell Adhesion and Growth," Chemistry and Biology, vol. 16, pp. 773-782, Jul. 31, 2009.
Supplementary European Search Report issued Apr. 20, 2012 in corresponding European Patent Application No. 09766649.9.

* cited by examiner

*Primary Examiner* — Sarah Pihonak
(74) *Attorney, Agent, or Firm* — Wenderoth, Lind & Ponack, L.L.P.

(57) ABSTRACT

The subject invention discloses an agent for promoting cell adhesion to a support, comprising a dispirotripiperazine derivative represented by Formula I below or a salt thereof; a method for promoting cell adhesion to a support comprising adding the dispirotripiperazine derivative represented by Formula I below or a salt thereof to a culture medium, or applying the same to a support; and an agonist of a heparin sulfate that comprises the dispirotripiperazine derivative represented by Formula I below or a salt thereof, and that promotes cell adhesion and/or cell growth.

12 Claims, 10 Drawing Sheets

CELL ADHESION PROMOTING AGENT AND METHOD OF PROMOTING CELL ADHESION

TECHNICAL FIELD

The present invention relates to a cell adhesion promoter containing a dispirotripiperazine derivative or a salt thereof, a method for promoting cell adhesion comprising adding the dispirotripiperazine derivative or a salt thereof to a culture medium or applying the same to a support, and a novel compound having a cell adhesion promoting effect.

BACKGROUND ART

Native extracellular matrices such as collagen have been used as coating materials when culturing difficult-to-culture cells, and have significantly contributed to basic studies of bioengineering and cell biology. However, the drawbacks of such natural animal-derived materials include the risk of disease transmission, low purity, and poor reproducibility and stability. These limitations can be overcome by the use of synthetic materials. However, such synthetic materials often show only a weaker adhesive effect than naturally derived materials.

Antiviral activity of some types of dispirotripiperazine derivatives has been reported in Non-Patent Literatures 1 and 2.

CITATION LIST

Non-Patent Literature

NPL 1: Schmidtke, M., Riabova, O., Dahse, H. M., Stelzner, A., Makarov, V., Synthesis, cytotoxicity and antiviral activity of N,N'-bis-5-nitropyrimidyl derivatives of dispirotripiperazine. Antiviral Research (2002), 55(1), 117-127.

NPL 2: Artemenko, A. G., Muratov, E. N., Kuz'min, V. E., Kovdienko, N. A., Hromov, A. I., Makarov, V. A., Riabova, O. B., Wutzler, P., Schmidtke, M. Identification of individual structural fragments of N,N'-(bis-5-nitropyrimidyl) dispirotripiperazine derivatives for cytotoxicity and antiherpetic activity allows the prediction of new highly active compounds. Journal of Antimicrobial Chemotherapy (2007), 60 (1), 68-77.

SUMMARY OF INVENTION

Technical Problems

The present invention provides a cell adhesion promoter that contains a dispirotripiperazine derivative or a salt thereof, and that promotes cell adhesion to a support. Further, the present invention provides a method for promoting cell adhesion to a support, comprising adding the dispirotripiperazine derivative or a salt thereof to a culture medium, or applying the same to a support. The present invention provides an agonist of heparan sulfate that promotes cell adhesion and/or cell growth. Further, the present invention provides a novel compound having an effect of promoting cell adhesion to a support.

Solutions to Problem

During screening of a library of synthetic compounds, the present inventors found that cell adhesion is promoted in the presence of a specific dispirotripiperazine derivative. The present invention is achieved by further studies based on the above finding, and provides a cell adhesion promoter, method for promoting cell adhesion, and an agonist of heparan sulfate and a novel compound that promote cell adhesion and/or cell growth.

[Item 1]

A cell adhesion promoter for promoting cell adhesion to a support, comprising a dispirotripiperazine derivative represented by Formula I below or a salt thereof,

[Chem. 1]

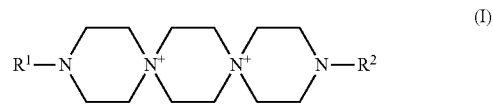

(I)

wherein $R^1$ and $R^2$ are the same or different, and each represent hydrogen, an alkyl group, an alkenyl group, an alkynyl group, a cycloalkyl group, a cycloalkylalkyl group, an aryl group, a heteroaryl group, an aryl-substituted alkyl group, a heteroaryl-substituted alkyl group (excluding the case where both $R^1$ and $R^2$ are hydrogen; $R^1$ and $R^2$ each being optionally derivatized with dansylhydrazine or bonded with a substance having integrin-binding activity; the alkyl group, the alkenyl group, the alkynyl group, and each alkyl moiety are optionally substituted with at least one atom or one group selected from halogen, hydroxyl (the hydroxy being optionally acylated, carbamated or etherified), cyano, nitro, amino, mono- or di-substituted amino, carbamoyl and sulfamoyl; the alkyl group, the alkenyl group, the alkynyl group, the cycloalkyl group, each alkyl moiety and each cycloalkyl moiety are optionally interrupted by —O—, —S—, —SO—, —SO$_2$—, —OSO$_2$—, —NH—, —CO—, —CH=CH—, —C≡C—, —CONH—, —NHCO—, —NHCOO—, —OCH$_2$CONH—, or —OCH$_2$CO—; and the aryl group, each aryl moiety, the heteroaryl group, each heteroaryl moiety, the cycloalkyl group and each cycloalkyl moiety are optionally substituted with at least one atom or one group selected from halogen, hydroxyl, formyl, alkyl, hydroxyalkyl, alkoxy, alkylthio, cyano, nitro, amino, mono- or di-substituted amino, carbamoyl, sulfamoyl, alkyl sulfonyl, alkyl sulfonylamino, alkyl carbonylamino, methylenedioxy, and aryl) or a group represented by Formula II below (excluding the case where both of $R^1$ and $R^2$ are a group represented by Formula II),

[Chem. 2]

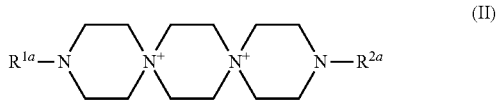

(II)

wherein $R^{1a}$ represents an alkylene group, an alkenylene group, an alkynylene group, a cycloalkylene group, a cycloalkylalkylene group, an arylene group, a heteroarylene group, an aryl-substituted alkylene group, or a heteroaryl-substituted alkylene group (the alkylene group, the alkenylene group, the alkynylene group, and each alkylene moiety being optionally substituted with at least one atom or one group selected from halogen, hydroxyl (the hydroxy being optionally acylated, carbamated or etherified), cyano, nitro, amino, mono- or di-substituted amino, carbamoyl and sulfamoyl; the alkylene group, the alkenylene group, the alkynylene group, the cycloalkylene group, each alkylene moiety and each cycloalkyl moiety are optionally interrupted by —O—, —S—, —SO—, —SO$_2$—, —OSO$_2$—, —NH—, —CO—, —CH=CH—, —C≡C—, —CONH—, —NHCO—, —NHCOO—, —OCH$_2$CONH—, or —OCH$_2$CO—; and the arylene group, each aryl moiety, the heteroarylene group, each heteroaryl moiety, the cycloalkylene group and each cycloalkyl moiety are optionally substituted with at least one atom or one group selected from halogen, hydroxyl, formyl, alkyl, hydroxyalkyl, alkoxy, alkylthio, cyano, nitro, amino, mono- or di-substituted amino, carbamoyl, sulfamoyl, alkyl sulfonyl, alkyl sulfonylamino, alkyl carbonylamino, methylenedioxy, and aryl); and R$^{2a}$ has the same definition as those of R$^1$ and R$^2$.

[Item 2]

The cell adhesion promoter according to Item 1, wherein the dispirotripiperazine derivative is selected from the groups below.

[Chem. 3]

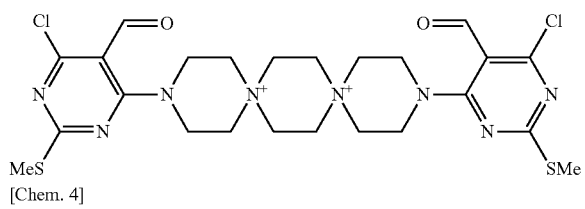

(a)

[Chem. 4]

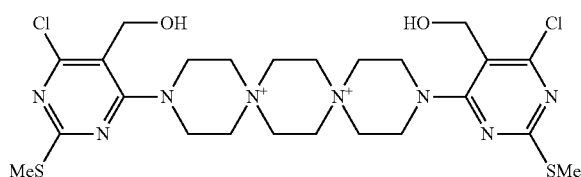

(b)

[Chem. 5]

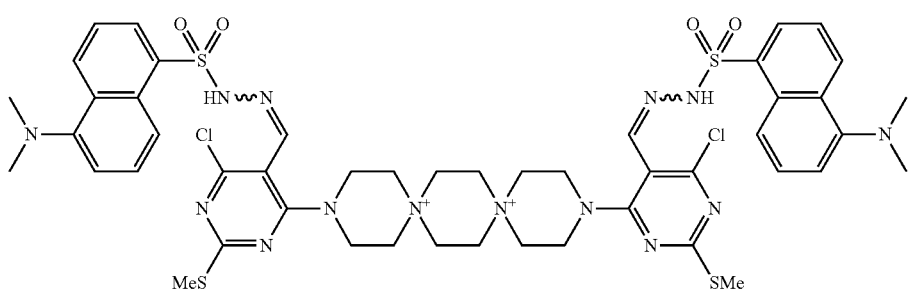

(c)

[Chem. 6]

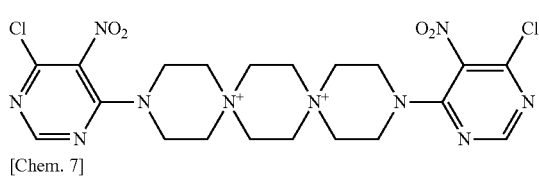

(d)

[Chem. 7]

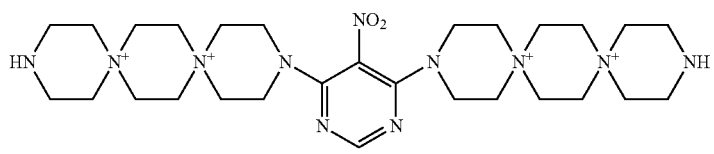

(e)

[Chem. 8]

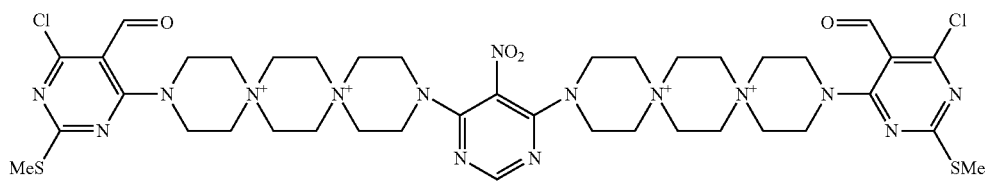

(f)

-continued

[Chem. 9]

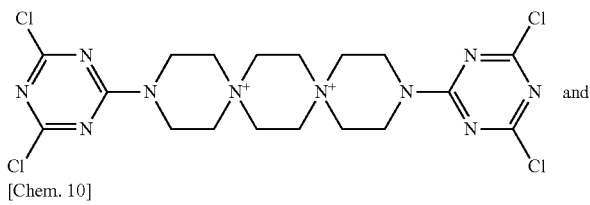

and (g)

[Chem. 10]

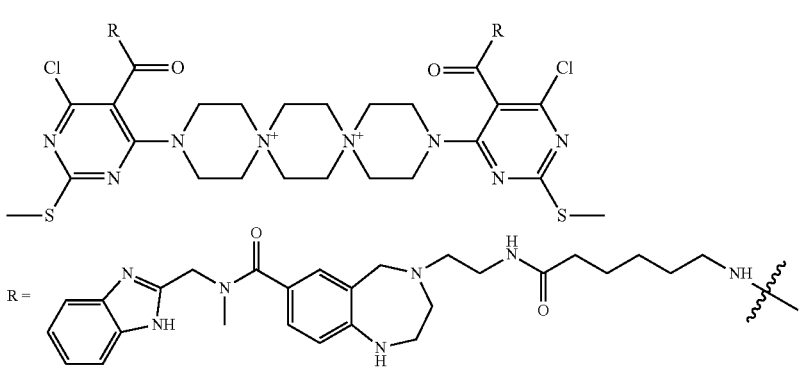

(h)

[Item 3]

The cell adhesion promoter according to Item 1 or 2, wherein the support is a cell culture vessel.

[Item 4]

The cell adhesion promoter according to any one of Item 1 to 3, wherein the cell is a nonadherent cell.

[Item 5]

A method for promoting cell adhesion to a support, comprising either adding the dispirotripiperazine derivative or a salt thereof according to Item 1 to a culture medium, or applying the dispirotripiperazine derivative or a salt thereof according to Item 1 to a support.

[Item 6]

A method for promoting cell adhesion to a support, comprising either adding the dispirotripiperazine derivative or a salt thereof according to Item 2 to a culture medium, or applying the dispirotripiperazine derivative or a salt thereof according to Item 2 to a support.

[Item 7]

The method according to Item 5 or 6, wherein the support is a cell culture vessel.

[Item 8]

The method according to any one of Item 5 to 7, wherein the cell is a nonadherent cell.

[Item 9]

An agonist of a heparan sulfate for promoting cell adhesion and/or cell growth, comprising the dispirotripiperazine derivative or a salt thereof according to Item 1 or 2.

[Item 10]

A dispirotripiperazine derivative represented by Formula Ia below or a salt thereof,

[Chem. 11]

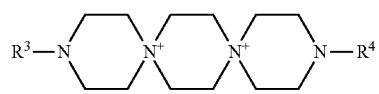

(Ia)

wherein $R^3$ and $R^4$ are the same or different, and each represent a monocyclic aryl group or a monocyclic heteroaryl group ($R^3$ and $R^4$ being optionally derivatized with dansylhydrazine or bonded with a substance having integrin-binding activity; and the aryl group and the heteroaryl group are optionally substituted with at least one atom or one group selected from halogen, hydroxyl formyl, alkyl, hydroxyalkyl, alkoxy, alkylthio, cyano, nitro, amino, mono- or di-substituted amino, carbamoyl, sulfamoyl, alkyl sulfonyl, alkyl sulfonylamino, alkyl carbonylamino, methylenedioxy, and aryl); or a group represented by Formula IIa below (excluding the case where $R^3$ and $R^4$ are the same, and are a 4-pyrimidyl group whose 5-position is substituted with a nitro group, an amino group, a formyl group, or an ethoxycarbonyl group, a 2-pyridyl group whose 3-position is substituted with a nitro group, or a phenyl group whose 2-position is substituted with a nitro group, and the case where both of $R^3$ and $R^4$ are a group represented by Formula IIa),

[Chem. 12]

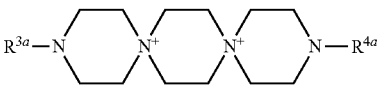

(IIa)

wherein $R^{3a}$ represents a monocyclic arylene group or monocyclic heteroarylene group, (the arylene group and heteroarylene group being optionally substituted with at least one atom or one group selected from halogen, hydroxyl, formyl, alkyl, hydroxyalkyl, alkoxy, alkylthio, cyano, nitro, amino, mono- or di-substituted amino, carbamoyl, sulfamoyl, alkyl sulfonyl, alkyl sulfonylamino, alkyl carbonylamino, methylenedioxy, and aryl), and $R^{4a}$ has the same definition as that of $R^3$ and $R^4$.

[Item 11]

A dispirotripiperazine derivative or a salt thereof selected from the groups below.

[Item 12]

Use of the dispirotripiperazine derivative or a salt thereof according to Item 1 or 2 for promoting cell adhesion to a support.

[Item 13]

A cell culture medium comprising the dispirotripiperazine derivative or a salt thereof according to Item 1 or 2.

[Chem. 13]

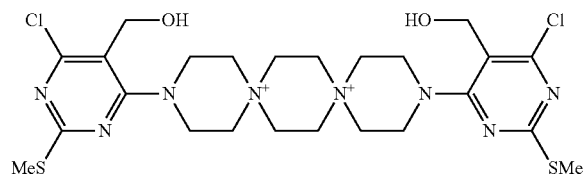

(b)

[Chem. 14]

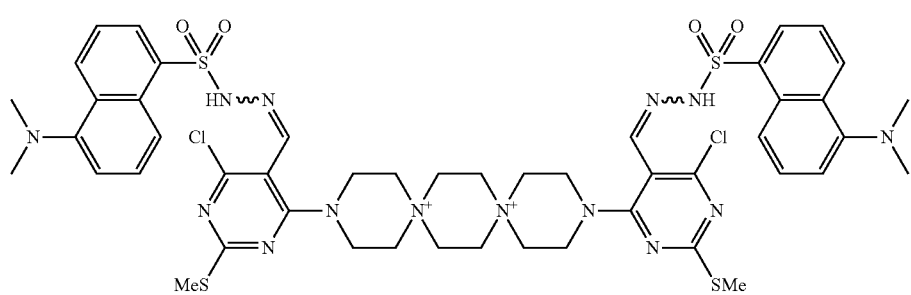

(c)

[Chem. 15]

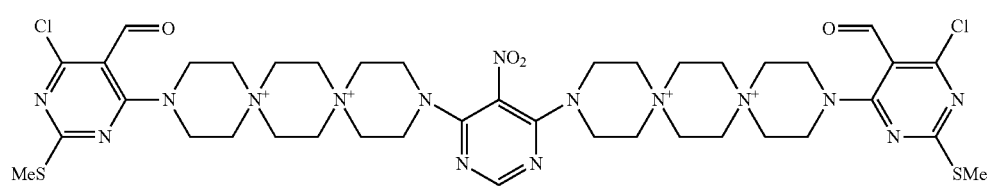

(f)

[Chem. 16]

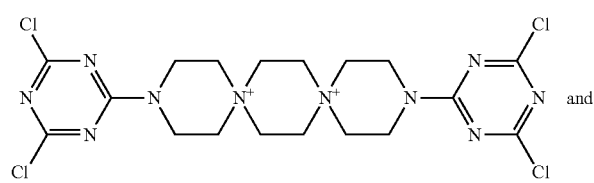

and (g)

[Chem. 17]

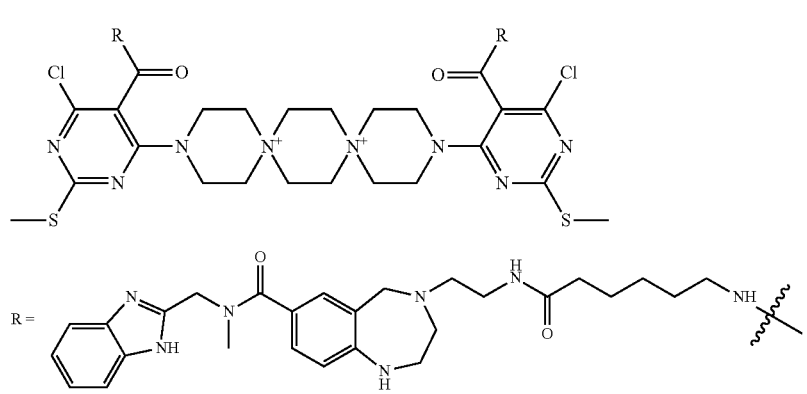

(h)

[Item 14]

A cell culture vessel to which the dispirotripiperazine derivative or a salt thereof according to Item 1 or 2 is applied.

Advantageous Effects of Invention

A dispirotripiperazine derivative represented by Formula I or a salt thereof of the present invention is a small molecule compound, which was found, for the first time, to exhibit an effect of promoting cell adhesion simply by being added to a culture medium.

In the presence of the dispirotripiperazine derivative represented by Formula I or a salt thereof of the present invention, adhesion of both non-adherent cells and anchorage-dependent cells to a support is promoted.

The dispirotripiperazine derivative represented by Formula I or a salt thereof of the present invention also functions as an agonist of heparan sulfate, and promotes cell adhesion and/or cell growth.

Further, a dispirotripiperazine derivative represented by Formula Ia is a novel compound that has an effect of promoting cell adhesion.

This cell adhesion promoting effect is reversible. It is noteworthy that adhesion of cells to a culture plate is strengthened simply by adding the above to a culture medium; however, cell-cell adhesion is not mediated.

DESCRIPTION OF EMBODIMENTS

Figure 1:
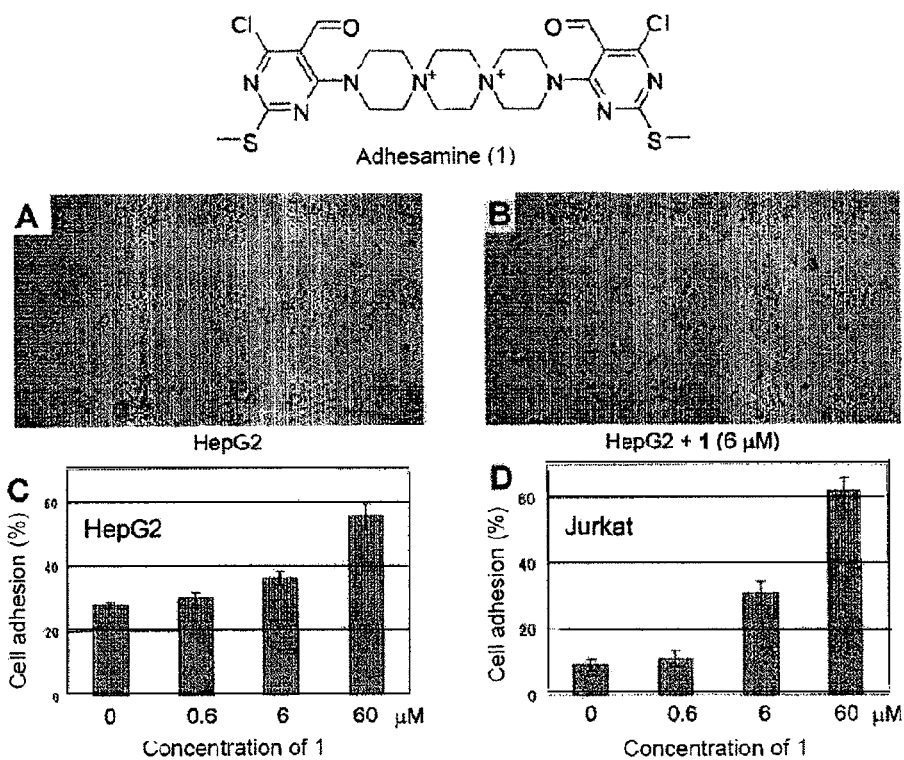
FIG. 1 (A) and (B) show micrographs of HepG2 cells incubated with 1% (v/v) DMSO alone (A) or in the presence of 6 μM adhesamine (B).
(C) and (D) are graphs showing adhesion rate of HepG2 cells (C) and Jurkat cells (D) in a culture media to which 0-60 μM of adhesamine is added.

Hereinbelow, a cell adhesion promoter, a method for promoting cell adhesion, and an agonist of heparan sulfate that promotes cell adhesion and/or cell growth of the present invention are described in detail.

Cell Adhesion Promoter

The cell adhesion promoter of the present invention that promotes cell adhesion to a support comprises a dispirotripiperazine derivative represented by Formula I below, or a salt thereof.

Dispirotripiperazine Derivative and Salt Thereof

[Chem. 18]

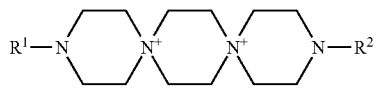

(I)

wherein $R^1$ and $R^2$ are the same or different, and each represent hydrogen, an alkyl group, an alkenyl group, an alkynyl group, a cycloalkyl group, a cycloalkylalkyl group, an aryl group, a heteroaryl group, an aryl-substituted alkyl group, a heteroaryl-substituted alkyl group (excluding the case where both $R^1$ and $R^2$ are hydrogen; $R^1$ and $R^2$ each being optionally derivatized with dansylhydrazine; the alkyl group, the alkenyl group, the alkynyl group, and each alkyl moiety are optionally substituted with at least one atom or one group selected from halogen, hydroxyl (the hydroxy being optionally acylated, carbamated or etherified), cyano, nitro, amino, mono- or di-substituted amino, carbamoyl and sulfamoyl; the alkyl group, the alkenyl group, the alkynyl group, the cycloalkyl group, each alkyl moiety and each cycloalkyl moiety are optionally interrupted by —O—, —S—, —SO—, —SO$_2$—, —OSO$_2$—, —NH—, —CO—, —CH=CH—, —C≡C—, —CONH—, —NHCO—, —NHCOO—, —OCH$_2$CONH—, or —OCH$_2$CO—; and the aryl group, each aryl moiety, the heteroaryl group, each heteroaryl moiety, the cycloalkyl group and each cycloalkyl moiety are optionally substituted with at least one atom or one group selected from halogen, hydroxyl, formyl, alkyl, hydroxyalkyl, alkoxy, alkylthio, cyano, nitro, amino, mono- or di-substituted amino, carbamoyl, sulfamoyl, alkyl sulfonyl, alkyl sulfonylamino, alkyl carbonylamino, methylenedioxy, and aryl) or a group represented by Formula II (excluding the case where both of $R^1$ and $R^2$ are a group represented by Formula II),

[Chem. 19]

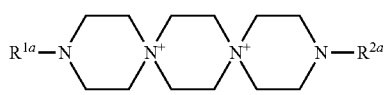

(II)

wherein $R^{1a}$ represents an alkylene group, an alkenylene group, an alkynylene group, a cycloalkylene group, a cycloalkylalkylene group, an arylene group, a heteroarylene group, an aryl-substituted alkylene group, or a heteroaryl-substituted alkylene group (the alkylene group, the alkenylene group, the alkynylene group, and each alkylene moiety being optionally substituted with at least one atom or one group selected from halogen, hydroxyl (the hydroxy being optionally acylated, carbamated or etherified), cyano, nitro, amino, mono- or di-substituted amino, carbamoyl and sulfamoyl; the alkylene group, the alkenylene group, the alkynylene group, the cycloalkylene group, each alkylene moiety and each cycloalkyl moiety are optionally interrupted by —O—, —S—, —SO—, —SO$_2$—, —OSO$_2$—, —NH—, —CO—, —CH=CH—, —C≡C—, —CONH—, —NHCO—, —NHCOO—, —OCH$_2$CONH—, or —OCH$_2$CO—; and the arylene group, each aryl moiety, the heteroarylene group, each heteroaryl moiety, the cycloalkylene group and each cycloalkyl moiety are optionally substituted with at least one atom or one group selected from halogen, hydroxyl, formyl, alkyl, hydroxyalkyl, alkoxy, alkylthio, cyano, nitro, amino, mono- or di-substituted amino, carbamoyl, sulfamoyl, alkyl sulfonyl, alkyl sulfonylamino, alkyl carbonylamino, methylenedioxy, and aryl); and $R^{2a}$ has the same definition as those of $R^1$ and $R^2$)).

The above dispirotripiperazine derivative may also be one to which a substance having integrin-binding activity, such as RGD (Arg-Gly-Asp) sequence, etc., is further coupled thereto via a linker or the like.

The salt of the dispirotripiperazine derivative represented by the above Formula I refers to a salt from two molecules of monovalent anion or one molecule of divalent anion with respect to one molecule of dispirotripiperazine derivative. Specific examples of such salts include inorganic acid salts such as hydrochloride, hydrobromate, hydroiodide, hydrosulfate, perchlorate, etc.; organic acid salts such as oxalate, malonate, succinate, maleate, fumarate, lactate, malate, tartrate, benzoate, trifluoroacetate, acetate, methanesulfonate, p-toluenesulfonate, trifluoromethanesulfonate, etc.; and acidic amino acid salts such as glutamate, aspartate, etc.

More specific examples of each group shown in the above Formula I are as follows:

The "alkyl group" may be linear, branched or cyclic. Examples thereof include methyl, ethyl, n-propyl, isopropyl, n-butyl, isobutyl, tert-butyl, n-pentyl, isopentyl, hexyl, heptyl, octyl, nonyl, and decyl. The carbon number is preferably 1 to 30, more preferably 1 to 20.

The "alkenyl group" may be linear, branched or cyclic, and has at least one double bond. Examples thereof include vinyl, allyl, 1-propenyl, 2-methyl-2-propenyl, isopropenyl, 1-, 2-, or 3-butenyl, 2-, 3-, or 4-pentenyl, 2-methyl-2-butenyl, 3-methyl-2-butenyl, 5-hexenyl, 1-cyclopentenyl, 1-cyclohexenyl, 3-methyl-3-butenyl, and equivalents thereof. The carbon number is preferably 2 to 30, more preferably 2 to 20.

The "alkynyl group" may be linear, branched or cyclic, and has at least one triple bond. Examples thereof include ethynyl, 1- or 2-propynyl, 1-, 2-, or 3-butynyl, 1-methyl-2-propynyl, and equivalents thereof. The carbon number is preferably 2 to 30, more preferably 2 to 20.

Specific examples of "cycloalkyl groups" include cyclopropyl, cyclobutyl, cyclopentyl, cyclohexyl, and cycloheptyl. The carbon number is preferably 3 to 8, more preferably 5 or 6.

The term "aryl group" refers to a monocyclic or polycyclic group that has a 5- or 6-membered aromatic hydrocarbon ring or rings. Specific examples thereof include phenyl, naphthyl, fluorenyl, anthryl, biphenylyl, tetrahydronaphthyl, chromanyl, 2,3-dihydro-1,4-dioxanaphthalenyl, indanyl, and phenanthryl.

The term "heteroaryl group" refers to a monocyclic or polycyclic group that has a 5- or 6-membered aromatic ring or rings containing 1 to 3 heteroatoms selected from N, O, and S. If it is polycyclic, at least one ring is an aromatic ring, and N is preferably situated adjacent to a carbon atom bound to another molecule. Specific examples thereof include furyl, thienyl, pyrrolyl, imidazolyl, pyrazolyl, oxazolyl, thiazolyl, isooxazolyl, isothiazolyl, pyridyl, pyrazinyl, pyrimidinyl, pyridazinyl, indolyl, quinolyl, isoquinolyl, benzo[b]thienyl, and benzimidazolyl.

The term "alkyl moiety" includes not only each alkyl group in a cycloalkylalkyl group, an aryl-substituted alkyl group, and a heteroaryl-substituted alkyl group, but also an alkyl group in hydroxyalkyl, alkylthio, alkylsulfonyl, alkylsulfonylamino, alkylcarbonylamino, and alkoxy (O-alkyl group) in an alkoxy group, as well as an alkyl group as a substituent in mono- or di-substituted amino, carbamoyl, and sulfamoyl groups.

The term "cycloalkyl moiety" refers to a cycloalkyl group of a cycloalkyl-alkyl group and a cycloalkylalkylene group.

The term "aryl moiety" refers to an aryl group in an aryl-substituted alkyl group and an aryl-substituted alkylene group.

The term "heteroaryl moiety" refers to a heteroaryl group in a heteroaryl-substituted alkyl group and a heteroaryl-substituted alkylene group.

Specific examples of compound groups containing an alkyl, cycloalkyl, aryl, or heteroaryl moiety may include those that have the above-described specific examples of each group at the corresponding moieties.

Specific examples of "cycloalkylalkyl groups" include cyclopropylmethyl, cyclobutylmethyl, cyclopentylmethyl, cyclohexylmethyl, and cycloheptylmethyl.

Specific examples of "aryl-substituted alkyl groups" include benzyl, naphthylmethyl, fluorenylmethyl, anthrylmethyl, biphenylylmethyl, tetrahydro naphthylmethyl, chromanylmethyl, 2,3-dihydro-1,4-dioxanaphthalenylmethyl, indanylmethyl, phenanthrylmethyl, phenethyl, naphthylethyl, fluorenylethyl, anthryl ethyl, biphenylylethyl, tetrahydro naphthylethyl, chromanylethyl, 2,3-dihydro-1,4-dioxanaphthalenylethyl, indanylethyl, and phenanthrylethyl.

Specific examples of "heteroaryl-substituted alkyl groups" include furylmethyl, thienylmethyl, pyrrolylmethyl, imidazolylmethyl, pyrazolylmethyl, oxazolylmethyl, thiazolylmethyl, isoxazolylmethyl, isothiazolylmethyl, pyridylmethyl, pyrazinylmethyl, pyrimidinylmethyl, pyridazinylmethyl, indolylmethyl, quinolylmethyl, isoquinolylmethyl, benzo[b]thienylmethyl, benzimidazolylmethyl, furylethyl, thienylethyl, pyrrolylethyl, imidazolylethyl, pyrazolylethyl, oxazolylethyl, thiazolylethyl, isooxazolylethyl, isothiazolylethyl, pyridylethyl, pyrazinylethyl, pyrimidinylethyl, pyridazinylethyl, indolylethyl, quinolylethyl, isoquinolylethyl, benzo[b]thienylethyl, and benzimidazolylethyl.

The term "dansylhydrazine derivatization" means a state in which a moiety is bound to dansylhydrazine as a result of a reaction with dansylhydrazine. Specific examples include compounds represented by Formula (c) below.

The term "halogen atom" means fluorine, chlorine, bromine, or iodine.

The term "acylated hydroxy" refers to alkylcarbonyloxy, arylcarbonyloxy, or aryl-substituted alkylcarbonyloxy.

The term "carbamated hydroxy" refers to alkylaminocarbonyloxy, arylaminocarbonyloxy, or aryl-substituted alkylaminocarbonyloxy.

The term "etherified hydroxy" refers to alkyloxy, aryloxy, or aryl-substituted alkyloxy.

Specific examples of alkylcarbonyloxy include methylcarbonyloxy, ethylcarbonyloxy, n-propylcarbonyloxy, isopropylcarbonyloxy, n-butylcarbonyloxy, isobutylcarbonyloxy, tert-butylcarbonyloxy, n-pentylcarbonyloxy, isopentylcarbonyloxy, and hexylcarbonyloxy.

Specific examples of arylcarbonyloxy include phenylcarbonyloxy, naphthylcarbonyloxy, fluorenylcarbonyloxy, anthrylcarbonyloxy, biphenylylcarbonyloxy, tetrahydronaphthylcarbonyloxy, chromanylcarbonyloxy, 2,3-dihydro-1,4-dioxanaphthalenylcarbonyloxy, indanylcarbonyloxy, and phenanthrylcarbonyloxy.

Specific examples of aryl-substituted alkylcarbonyloxy include benzylcarbonyloxy, naphthylmethylcarbonyloxy, fluorenylmethylcarbonyloxy, anthrylmethylcarbonyloxy, biphenylylmethylcarbonyloxy, tetrahydronaphthylmethylcarbonyloxy, chromanylmethylcarbonyloxy, 2,3-dihydro-1,4-dioxanaphthalenylmethylcarbonyloxy, indanylmethylcarbonyloxy and phenanthrylmethylcarbonyloxy, phenethylcarbonyloxy, naphthylethylcarbonyloxy, fluorenylethylcarbonyloxy, anthrylethylcarbonyloxy, biphenylylethylcarbonyloxy, tetrahydronaphthylethylcarbonyloxy, chromanylethylcarbonyloxy, 2,3-dihydro-1,4-dioxanaphthalenylethylcarbonyloxy, indanylethylcarbonyloxy, and phenanthrylethylcarbonyloxy.

Specific examples of alkylaminocarbonyloxy include methylaminocarbonyloxy, ethylaminocarbonyloxy, n-propylaminocarbonyloxy, isopropylaminocarbonyloxy, n-butylaminocarbonyloxy, isobutylaminocarbonyloxy, tert-butylaminocarbonyloxy, n-pentylaminocarbonyloxy, isopentylaminocarbonyloxy, and hexylaminocarbonyloxy.

Specific examples of arylaminocarbonyloxy include phenylaminocarbonyloxy, naphthylaminocarbonyloxy, fluorenylaminocarbonyloxy, anthrylaminocarbonyloxy, biphenylylaminocarbonyloxy, tetrahydronaphthylaminocarbonyloxy, chromanylaminocarbonyloxy, 2,3-dihydro-1,4-dioxanaphthalenylaminocarbonyloxy, indanylaminocarbonyloxy, and phenanthrylaminocarbonyloxy.

Specific examples of aryl-substituted alkylaminocarbonyloxy include benzylaminocarbonyloxy, naphthylmethylaminocarbonyloxy, fluorenylmethylaminocarbonyloxy, anthrylmethylaminocarbonyloxy, biphenylylmethylaminocarbonyloxy, tetrahydronaphthylmethylaminocarbonyloxy, chromanylmethylaminocarbonyloxy, 2,3-dihydro-1,4-dioxanaphthalenylmethylaminocarbonyloxy, indanylmethylaminocarbonyloxy and phenanthrylmethylaminocarbonyloxy, phenethylaminocarbonyloxy, naphthylethylaminocarbonyloxy, fluorenylethylaminocarbonyloxy, anthrylethylaminocarbonyloxy, biphenylylethylaminocarbonyloxy, tetrahydronaphthylethylaminocarbonyloxy, 2,3-dihydro-1,4-dioxanaphthalenylethylaminocarbonyloxy, indanylethylaminocarbonyloxy, and phenanthrylethylaminocarbonyloxy.

Specific examples of alkyloxy include methyloxy, ethyloxy, n-propyloxy, isopropyloxy, n-butyloxy, isobutyloxy, tert-butyloxy, n-pentyloxy, isopentyloxy, and hexyloxy.

Specific examples of aryloxy include phenyloxy, naphthyloxy, fluorenyloxy, anthryloxy, biphenylyloxy, tetrahydronaphthyloxy, chromanyloxy, 2,3-dihydro-1,4-dioxanaphthalenyloxy, indanyloxy, and phenanthryloxy.

Specific examples of aryl-substituted alkyloxy include benzyloxy, naphthylmethyloxy, fluorenylmethyloxy, anthrylmethyloxy, biphenylylmethyloxy, tetrahydronaphthylmethyloxy, chromanylmethyloxy, 2,3-dihydro-1,4-dioxanaphthalenylmethyloxy, indanylmethyloxy and phenanthrylmethyloxy, phenethyloxy, naphthylethyloxy, fluorenylethyloxy, anthrylethyloxy, biphenylylethyloxy, tetrahydronaphthylethyloxy, chromanylethyloxy, 2,3-dihydro-1,1-dioxanaphthalenylethyloxy, indanylethyloxy, and phenanthrylethyloxy.

The term "mono-substituted" as in a mono- or di-substituted amino group, a mono- or di-substituted carbamoyl group, or a mono- or di-substituted sulfamoyl group means that one of the hydrogen atoms bound to the nitrogen atom of the amino group, the carbamoyl group, or the sulfamoyl group is substituted by alkyl. The term "di-substituted" means that two of the hydrogen atoms bound to the nitrogen atom of the amino group, the carbamoyl group, or the sulfamoyl group are substituted by the same or different alkyl.

Examples of amino groups mono-substituted by alkyl include methylamino, ethylamino, n-propylamino, isopropylamino, n-butylamino, isobutylamino, tert-butylamino, n-pentylamino, isopentylamino, and hexylamino.

Examples of amino groups di-substituted by alkyl include dimethylamino, diethylamino, di-n-propylamino, diisopropylamino, di-n-butylamino, diisobutylamino, di-tert-butylamino, di-n-pentylamino, diisopentylamino, and dihexylamino.

Examples of carbamoyl groups mono-substituted by alkyl include methylcarbamoyl, ethylcarbamoyl, n-propylcarbamoyl, isopropylcarbamoyl, n-butylcarbamoyl, isobutylcarbamoyl, tert-butylcarbamoyl, n-pentylcarbamoyl, isopentylcarbamoyl, and hexylcarbamoyl.

Examples of carbamoyl groups di-substituted by alkyl include dimethylcarbamoyl, diethylcarbamoyl, di-n-propylcarbamoyl, diisopropylcarbamoyl, di-n-butylcarbamoyl, diisobutylcarbamoyl, di-tert-butylcarbamoyl, di-n-pentylcarbamoyl, diisopentylcarbamoyl, and dihexylcarbamoyl.

Examples of sulfamoyl groups mono-substituted by alkyl include methylsulfamoyl, ethylsulfamoyl, n-propylsulfamoyl, isopropylsulfamoyl, n-butylsulfamoyl, isobutylsulfamoyl, tert-butylsulfamoyl, n-pentylsulfamoyl, isopentylsulfamoyl, and hexylsulfamoyl.

Examples of sulfamoyl groups di-substituted by alkyl include dimethylsulfamoyl, diethylsulfamoyl, di-n-propylsulfamoyl, diisopropylsulfamoyl, di-n-butylsulfamoyl, diisobutylsulfamoyl, di-tert-butylsulfamoyl, di-n-pentylsulfamoyl, diisopentylsulfamoyl, and dihexylsulfamoyl.

"The alkyl group, the alkenyl group, the alkynyl group, the cycloalkyl group, each alkyl moiety and each cycloalkyl moiety interrupted by —O—, —S—, —SO—, —SO$_2$—, —OSO$_2$—, —NH—, —CO—, —CH=CH—, —C≡C—, —CONH—, —NHCO—, —NHCOO—, —OCH$_2$CONH—, or —OCH$_2$CO—" refers to an alkyl group having at least two carbons, an alkenyl group having at least three carbons, an alkynyl group having at least three carbons, a cycloalkyl group, an alkyl moiety having at least two carbons and a cycloalkyl moiety, which are interrupted by —O—, —S—, —SO—, —SO$_2$—, —OSO$_2$—, —NH—, —CO—, —CH=CH—, —C≡C—, —CONH—, —NHCO—, —NHCOO—, —OCH$_2$CONH—, or —OCH$_2$CO—, in a carbon-carbon single bond in the alkyl group, the alkenyl group, the alkynyl group, the cycloalkyl group, the alkyl moiety and the cycloalkyl moiety. These are preferably bound to a carbon atom located two carbon atoms away from the nitrogen atom of dispirotripiperazine.

Specific examples of "hydroxyalkyl groups" include hydroxymethyl, hydroxyethyl, hydroxy-n-propyl, hydroxyisopropyl, hydroxy-n-butyl, hydroxyisobutyl, hydroxy-tert-butyl, hydroxy-n-pentyl, hydroxyisopentyl, and hydroxyhexyl.

Specific examples of "alkoxy groups" include methoxy, ethoxy, propoxy, isopropoxy, butoxy, isobutoxy, tert-butoxy, pentyloxy, isopentyloxy, and hexyloxy.

Specific examples of "alkylthio groups" include methylthio, ethylthio, n-propylthio, isopropylthio, n-butylthio, isobutylthio, tert-butylthio, n-pentylthio, isopentylthio, and hexylthio.

Specific examples of "alkylsulfonyl groups" include methylsulfonyl and ethylsulfonyl.

Specific examples of "alkylsulfonylamino groups" include methylsulfonylamino and ethylsulfonylamino.

Specific examples of "alkylcarbonylamino groups" include methylcarbonylamino and ethylcarbonylamino.

The "alkylene group" may be linear, branched or cyclic. Examples thereof include methylene, ethylene, n-propylene, isopropylene, n-butylene, isobutylene, tert-butylene, n-pentylene, isopentylene, hexylene, heptylene, octylene, nonylene, and decylene. The carbon number is preferably 1 to 30, more preferably 1 to 20.

The "alkynylene group" may be linear, branched or cyclic, and has at least one double bond. Examples thereof include vinylene, allylene, 1-propenylene, 2-methyl-2-propenylene, isopropenylene, 1-, 2-, or 3-butenylene, 2-, 3-, or 4-pentenylene, 2-methyl-2-butenylene, 3-methyl-2-butenylene, 5-hexenylene, 1-cyclopentenylene, 1-cyclohexenylene, 3-methyl-3-butenylene, and equivalents thereof. The carbon number is preferably 2 to 30, more preferably 2 to 20.

The "alkynylene group" may be linear, branched or cyclic, and has at least one triple bond. Examples thereof include ethynylene, 1- or 2-propynylene, 1-, 2-, or 3-butynylene, 1-methyl-2-propynylene, and equivalents thereof. The carbon number is preferably 2 to 30, more preferably 2 to 20.

Specific examples of "cycloalkylene groups" include cyclopropylene, cyclobutylene, cyclopentylene, cyclohexylene, and cycloheptylene. The carbon number is preferably 3 to 8, more preferably 5 or 6.

The term "arylene group" refers to a monocyclic or polycyclic group that has a 5- or 6-membered aromatic hydrocarbon ring or rings. Specific examples thereof include phenylene and naphthylene.

The term "heteroarylene group" refers to a monocyclic or polycyclic group that has a 5- or 6-membered aromatic ring or rings containing 1 to 3 heteroatoms selected from N, O, and S. If it is polycyclic, at least one ring is an aromatic ring, and N is preferably situated adjacent to a carbon atom bound to another molecule. Specific examples thereof include furylene and thienylene.

The term "alkylene moiety" refers to each alkylene group in a cycloalkylalkylene group, an aryl-substituted alkylene group, and a heteroaryl-substituted alkylene group.

Specific examples of compound groups containing alkylene may include those that have the above-described specific examples of each group at the corresponding moieties.

Specific examples of "cycloalkylalkylene groups" include cyclopropylmethylene, cyclobutylmethylene, cyclopentylmethylene, cyclohexylmethylene, and cycloheptylmethylene.

Specific examples of "aryl-substituted alkylene groups" include naphthylmethylene, fluorenylmethylene, anthrylmethylene, biphenylylmethylene, tetrahydronaphthylmethylene, chromanylmethylene, 2,3-dihydro-1,4-dioxanaphthalenylmethylene, indanylmethylene, phenanthrylmethylene, naphthylethylene, fluorenylethylene, anthrylethylene, biphenylylethylene, tetrahydronaphthylethylene, chromanylethylene, 2,3-dihydro-1,4-dioxanaphthalenylethylene, indanylethylene, and phenanthrylethylene.

Specific examples of "heteroaryl-substituted alkylene groups" include furylmethylene, thienylmethylene, pyrrolylmethylene, imidazolylmethylene, pyrazolylmethylene, oxazolylmethylene, thiazolylmethylene, isooxazolylmethylene, isothiazolylmethylene, pyridylmethylene, pyrazinylmethylene, pyrimidinylmethylene, pyridazinylmethylene, indolylmethylene, quinolylmethylene, isoquinolylmethylene, benzo[b]thienylmethylene, benzimidazolylmethylene, furylethylene, thienylethylene, pyrrolylethylene, imidazolylethylene, pyrazolylethylene, oxazolylethylene, thiazolylethylene, isooxazolylethylene, isothiazolylethylene, pyridylethylene, pyrazinylethylene, pyrimidinylethylene, pyridazinylethylene, indolylethylene, quinolylethylene, isoquinolylethylene, benzo[b]thienylethylene, and benzimidazolylethylene.

"The alkylene group, the alkenylene group, the alkynylene group, the cycloalkylene group, each alkylene moiety and each cycloalkyl moiety interrupted by —O—, —S—, —SO—, —SO$_2$—, —OSO$_2$—, —NH—, —CO—, —CH=CH—, —C≡C—, —CONH—, —NHCO—, —NHCOO—, —OCH$_2$CONH—, or —OCH$_2$CO—" refers to an alkylene group having at least two carbons, an alkenylene group having at least three carbons, an alkynylene group having at least three carbons, a cycloalkylene group, an alkylene moiety having at least two carbons and a cycloalkyl moiety, which are interrupted by —O—, —S—, —SO—, —SO$_2$—, —OSO$_2$—, —NH—, —CO—, —CH=CH—, —C≡C—, —CONH—, —NHCO—, —NHCOO—, —OCH$_2$CONH—, or —OCH$_2$CO—, in a carbon-carbon single bond in the alkylene group, the alkenylene group, the alkynylene group, the cycloalkylene group, the alkylene moiety, and the cycloalkyl moiety. These are preferably bound to a carbon atom located two carbon atoms away from the nitrogen atom of dispirotripiperazine.

Among the dispirotripiperazine derivatives of the present invention, specific examples of particularly preferable compounds include the following compounds, and salts thereof. Among them, compounds represented by Formulae (a) and (g) are particularly preferable. A compound represented by Formula (h) is a compound to which a substance having integrin-binding activity is bound.

[Chem. 20]

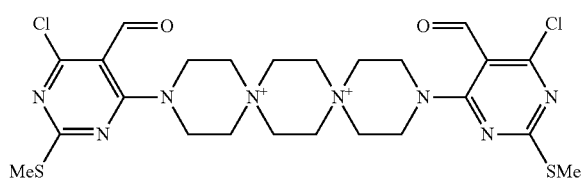

(a)

[Chem. 21]

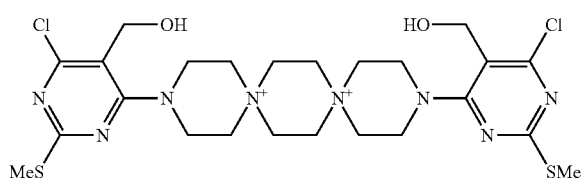

(b)

[Chem. 22]

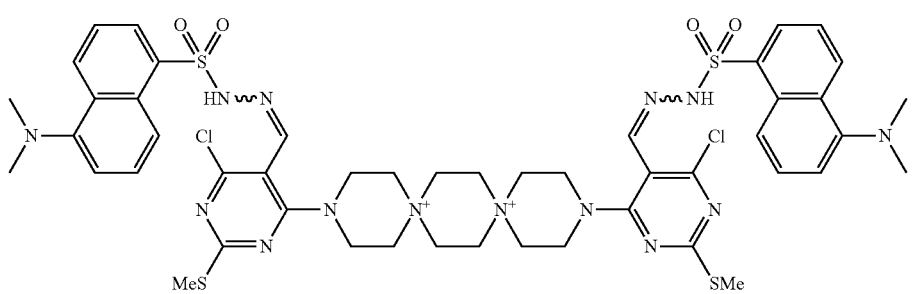

(c)

[Chem. 23]

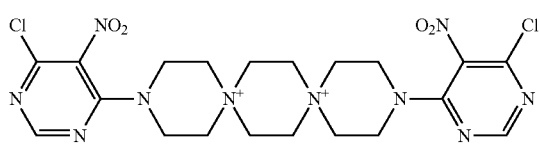

(d)

[Chem. 24]

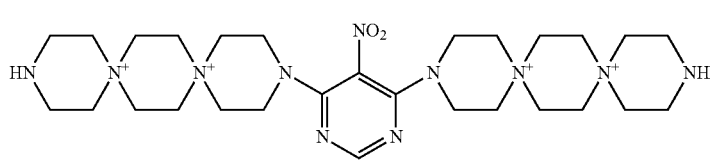

(e)

-continued

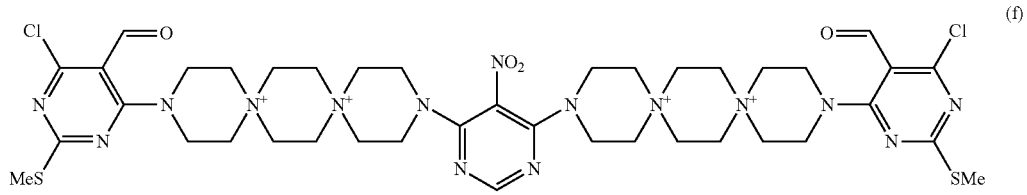
(f)

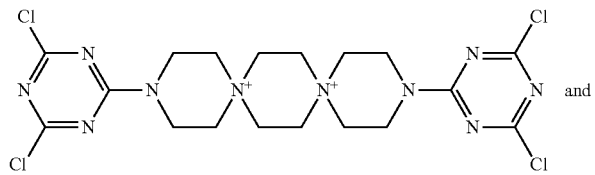
and
(g)

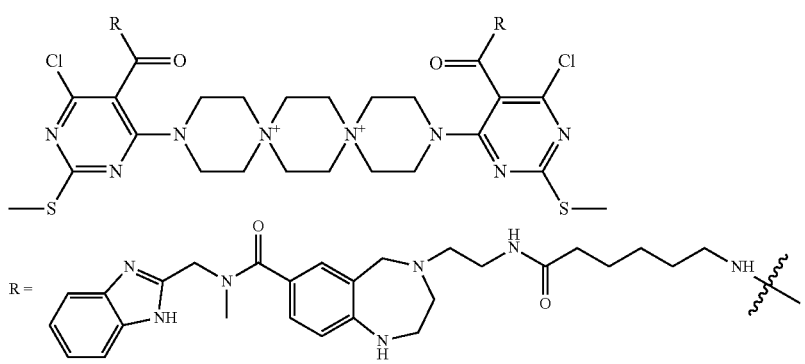
(h)

Effective Concentration and Amount

The effective concentration of the above-described dispirotripiperazine derivatives or salts thereof for causing cell adhesion to a support by being added to a culture medium is preferably about 0.4 to 400 μM in the culture medium, more preferably about 0.4 to 60 μM in the culture medium.

The effective amount of the dispirotripiperazine derivative represented by Formula I or a salt thereof for causing cell adhesion to a support by coating the support is preferably about 0.03 to 36.3 pmol/cm$^2$, more preferably about 0.30 to 36.3 pmol/cm$^2$.

Support

A support to which cells are adhered by using the cell adhesion promoter of the present invention is usually a plastic or glass material, and is not particularly limited insofar as it is a cell culture vessel for culturing cells or a medical material to be inserted into the body. Examples of such cell culture vessels include 12, 24, 48, and 96 multi-well plates for culturing, petri dishes for culturing, and flasks for culturing. These cell culture vessels may be either for tissue culture or suspension culture. A medical material to be inserted into the body is used for an artificial organ to be embedded in the body. Examples of artificial organs include artificial joints, artificial blood vessels, etc.

Cells

Target cells whose adhesion is promoted by using the cell adhesion promoter of the present invention are not particularly limited insofar as their adhesion to a support is promoted by using the cell adhesion promoter of the present invention, and are preferably animal cells, more preferably mammal cells. Examples thereof include cells derived from human, mouse, rat, etc. Further, in regard to the cell type, cells containing glycosaminoglycans on the cell surface are preferable, and cells containing heparin, heparan sulfate, or keratan sulfate as a glycosaminoglycan are particularly preferable. Cells may be either anchorage-dependent cells or non-adherent cells. The term "anchorage-dependent cells" used herein means cells that cannot survive and grow without being adhered to a culture vessel. Examples thereof include fibroblasts, epithelial cells, endothelial cells, smooth muscle cells, epidermal cells, hepatocytes, osteoblast cells, skeletal muscle cells, embryonic stem cells (ES cells), induced pluripotent stem cells (iPS cells), etc. The term "non-adherent cells" mean cells that can grow even in a floating state. Examples thereof include bone marrow cells, lymphoid cells, ascites cancer cells, etc. Further, cells to be used in the present invention may also be primary cultured cells, and the primary cultured cells may be derived from any tissues.

In regard to a culture medium used for culturing cells, a culture medium suitable for the cell type may be suitably selected and used. For example, a usable culture medium may be a known basal culture medium for culturing cells, such as Dulbecco's modified Eagle's medium, Williams' E medium, Ham's F-10 medium, F-12 medium, RPMI-1640 medium, MCDB 153 medium, 199 medium, etc., to which known growth factor, antioxidant agent, and the like suitable for culturing each cell type are added, if necessary. Further, the culture medium for culturing cells may be either a serum-added culture medium or a serum-free culture medium.

Method for Promoting Cell Adhesion

A method of the present invention for promoting cell adhesion to a support comprises adding the dispirotripiperazine derivative represented by the above Formula I or a salt thereof to a culture medium, or applying the same to a support.

As a preferable specific example, an embodiment of the method of the present invention for promoting cell adhesion to a support includes adding the dispirotripiperazine derivatives represented by the above Formulae (a) to (h) or salts thereof to a culture medium, or applying the same to a support; and further preferably includes adding the compounds represented by Formulae (a) and (g) or salts thereof to a culture medium, or applying the same to a support.

The above-described support can be used as the support for the method of the present invention for promoting cell adhesion to a support.

The above-described cells can be used as the cells used for the method of the present invention for promoting cell adhesion to a support.

The effective concentration of the above dispirotripiperazine derivatives or salts thereof for promoting cell adhesion is, in culture, preferably about 0.4 to 400 µM, more preferably about 0.4 to 60 µM; and on the support, preferably about 0.03 to 36.3 pmol/cm$^2$, more preferably about 0.30 to 36.3 pmol/cm$^2$.

Agonist of Cell Adhesion and/or Cell Growth Via Heparan Sulfate

The agonist of heparan sulfate of the present invention, which promotes cell adhesion and/or cell growth, comprises the dispirotripiperazine derivative represented by the above Formula I or a salt thereof.

Heparan sulfate is widely distributed as a universal component of cell membranes, and in a form of proteoglycan in which the heparan sulfate is bound to a protein. The above dispirotripiperazine derivative functions as an agonist by binding to heparan sulfate on cell membranes, and can induce cell adhesion and/or cell growth.

The agonist of heparan sulfate of the present invention, which promotes cell adhesion and/or cell growth, preferably comprises the dispirotripiperazine derivatives or salts thereof represented by the above Formulae (a) to (h), and further preferably comprises the dispirotripiperazine derivatives represented by the above Formulae (a) and (g), or salts thereof.

The agonist may be applied to any cell insofar as the cell contains heparan sulfate on the cell membrane. The above-described support can be used as the support for culturing cells.

The amount of the agonist to be added for culturing cells is preferably about 0.4 to 400 µM in a culture medium, more preferably about 0.4 to 60 µM in a culture medium, in terms of the effective concentration of the above dispirotripiperazine derivatives or salts thereof. The amount of the agonist for coating the support for culturing cells is preferably about 0.03 to 36.3 pmol/cm$^2$, more preferably about 0.30 to 36.3 pmol/cm$^2$, in terms of the effective amount of the above dispirotripiperazine derivatives or salts thereof.

Other Applications of Dispirotripiperazine Derivatives

Because the dispirotripiperazine derivative represented by the above Formula I or a salt thereof has activity to promote adhesion to a support, it can increase microinjection success rates by being added to a culture medium during microinjection into non-adherent cells. This facilitates introduction of a gene into non-adherent cells by microinjection.

Method for Preparing Dispirotripiperazine Derivatives and Salts Thereof

The compound represented by Formula I and a salt thereof can be prepared, for example, by reacting a compound of Formula III shown below with $R^1$—$X^1$ and $R^2$—$X^2$ (each of $X^1$ and $X^2$ is the same or different leaving group, and examples thereof include halogens such as Cl, Br, etc., and p-toluenesulfonyloxy, methanesulfonyloxy, etc.), and converting, if necessary, the resulting product into another compound of Formula I.

[Chem. 28]

(III)

The reaction of the compound of Formula III with the reactive derivatives of $R^1$ and $R^2$ is carried out in a solvent or without a solvent. A solvent to be used should be selected according to the type of starting compounds and the like. Examples thereof include toluene, tetrahydrofuran, dioxane, ethylene glycol diethyl ether, dichloromethane, chloroform, ethyl acetate, acetone, acetonitrile, dimethylformamide, 1,3-dimethyl-2-imidazolidinone, and 1-methyl-2-pyrrolidinone. These solvents are used alone, or in a combination of two or more thereof.

This reaction is carried out in the presence of a base, if necessary. Specific examples of bases include organic bases such as triethylamine, ethyldiisopropylamine, N-methylmorpholine, pyridine, and 4-dimethylaminopyridine.

The reaction temperature and the reaction time vary depending on the types of the starting materials and the like. The reaction temperature is usually about 0° C. to about 150° C., and the reaction time is usually about 0.5 hours to about 72 hours.

The molar ratio of the compound of Formula III to the reactive derivatives of $R^1$ and $R^2$ during reaction varies depending on the types of the starting materials and the like. It is usually 1:1.2 to 1:20, more preferably 1:2 to 1:10.

When producing a compound in which dispirotripiperazine is bound to another such dispirotripiperazine such as the dispirotripiperazine derivative represented by Formula (e), the compound of the above Formula III is reacted with $R^{1a}$—$X^1X^2$ ($X^1$ and $X^2$ are as defined above), and the resulting product is converted, if necessary, into the compound of Formula I in which a different dispirotripiperazine derivative is bound to another such dispirotripiperazine derivative. Thereby, the desired compound can be produced.

In this case, the molar ratio of the compound of Formula III and the reactive derivative of $R^{1a}$ during reaction varies depending on the types of the starting materials and the like. It is usually 600:1 to 2:1, more preferably 200:1 to 2:1.

When functional groups involved in the reaction are present in $R^1$, $R^2$, and $R^{1a}$ structures, preferably, these functional groups are protected according to conventional methods, followed by removal of the protective groups after the reaction.

Among the starting compounds used in the above-described production method, the compound of Formula III and the reactive derivatives of $R^1$, $R^2$, and $R^{1a}$ can be produced by a method known per se, or can be easily obtained because they are commercially available.

Dansylhydrazine derivatization may be carried out after the compound of the above Formula III is reacted with the reactive derivatives of $R^1$, $R^2$, and $R^{1a}$. This reaction can be carried out under reaction conditions usually used in the reaction of dansylhydrazine derivatization.

After the compound of the above Formula III is reacted with 4,6-dichloro-2-(methylthio)pyrimidine-5-carboxylic acid, the carboxylate moiety is converted to an active ester, and an RGD (arginine-glycine-asparagine) peptide derivative, an RGD peptide mimic, and the like are reacted, thereby causing a substance having integrin-binding activity to bind to adhesamine. This reaction can be carried out under reaction conditions usually used in the coupling reaction of active ester to amine.

The compound of Formula I produced by the above-described production methods or a production method in accordance with these methods can be isolated and purified according to conventional methods such as chromatography, recrystallization, reprecipitation, etc. The resulting compound is treated with various acids according to conventional methods so as to form a salt. Further, the compound of Formula I can be obtained in the form of salt depending on reaction and/or treatment conditions and the like; however, this salt can be converted to the compound of Formula I according to conventional methods.

EXAMPLES

The present invention is more specifically explained below in reference to Examples and Test Examples. The present invention is, however, not limited to those examples etc.

Example 1

[Chem. 29]

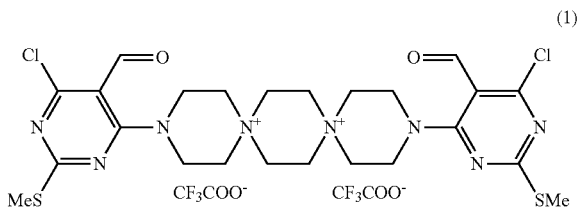

(1)

Adhesamine (1) ditrifluoroacetate was synthesized by adding 100 μL of an aqueous solution of 3,12-diaza-6,9-diazoniadispiro-(5,2,5,2)-hexadecane dibromide (7.5 mg, 19.4 μmol) and 6 μL of triethylamine to 4,6-dichloro-2-(methylthio)-5-formylpyrimidine (9.5 mg, 42.7 μmol) dissolved in 250 μL of dioxane. After stirring at room temperature for 3 hours, 500 μL of acetone was added. The resulting white precipitate was washed with acetone and purified by a reversed-phase HPLC (GL Sciences, Inc., Inertsil ODS-3, 4.6 mm×150 mm, flow rate 1.0 mL/min, 0.1% TFA MeOH/H$_2$O, 0→100%) to give adhesamine (1) ditrifluoroacetate as a white solid (11.1 mg, 69% yield). $^1$H NMR (300 MHz, CD$_3$OD) δ 2.58 (s, 6H), 3.82-4.12 (m, 16H), 4.24-4.31 (m, 8H), 10.3 (s, 2H); $^{13}$C NMR (150 MHz, DMSO-d$_6$) δ 14.7, 37.6, 42.2, 51.8, 108.1, 161.9, 164.6, 174.2, 187.8; FABMS (NBA) [M$^{2+}$] m/z=299; HRMS (FAB) calcd. for C$_{24}$H$_{32}$Cl$_2$N$_8$O$_2$S$_2$ [M$^{2+}$] m/z=299.0734, found 299.0724.

Example 2

[Chem. 30]

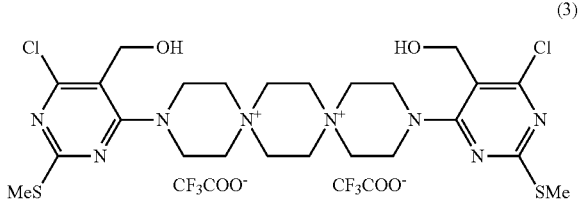

(3)

Compound (3) ditrifluoroacetate was synthesized by adding sodium tetrahydroborate (0.6 mg, 16.7 μmol) to adhesamine dichloride (1: 5.8 mg, 8.6 μmol) in 100 μL of methanol, and stirring the reaction mixture at room temperature for 30 minutes. 500 μL of acetone was added to the reaction mixture. The resulting white precipitate was washed with acetone and purified by a reversed-phase HPLC (GL Sciences, Inc., Inertsil ODS-3, 4.6 mm×150 mm, flow rate 1.0 mL/min, 0.1% TFA MeOH/H$_2$O, 0→100%) to give Compound (3) ditrifluoroacetate (3.8 mg, 56% yield) as a white solid. $^1$H NMR (300 MHz, CD$_3$OD) δ 2.57 (s, 6H), 3.97 (m, 8H), 4.25 (m, 16H), 4.67 (s, 4H); FABMS (NBA) [M$^{2+}$] m/z=301; HRMS (FAB) calcd. for C$_{24}$H$_{36}$Cl$_2$N$_8$O$_2$S$_2$ [M$^{2+}$] m/z=301.0890, found 301.0897.

Example 3

[Chem. 31]

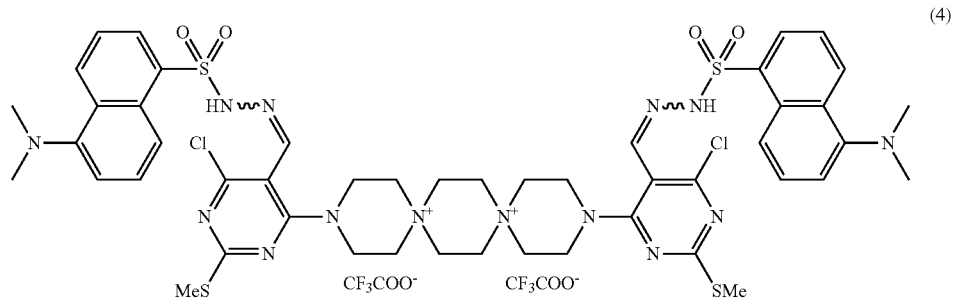

(4)

Compound (4) ditrifluoroacetate was synthesized by mixing adhesamine dichloride (1: 3.0 mg, 4.5 µmol) with dansyl hydrazine (2.3 mg, 8.6 µmol) in methanol containing 0.1% TFA, and heating the mixture at 65° C. for 3 hours. 500 µL of acetone was added to the reaction mixture, and the resulting white precipitate was washed with acetone and purified by a reversed-phase HPLC (GL Sciences, Inc., Inertsil ODS-3, 4.6 mm×150 mm, flow rate 1.0 mL/min, 0.1% TFA MeOH/H$_2$O, 0→100%) to give Compound (4) ditrifluoroacetate as a white solid (2.4 mg, 49% yield). $^1$H NMR (300 MHz, CD$_3$OD) δ 2.55 (s, 6H), 2.91 (s, 12H), 4.04-4.07 (m, 16H), 4.28-4.30 (m, 8H), 7.32 (d, J=8.1 Hz, 2H), 7.61 (t, J=8.1 Hz, 2H), 7.66 (t, J=7.6 Hz, 2H), 8.27 (s, 2H), 8.31 (d, J=7.6, 2H), 8.40 (d, J=7.6, 2H), 8.63 (d, J=8.1, 2H); FABMS (NBA) [M$^{2+}$] m/z=546; HRMS (FAB) calcd. for C$_{48}$H$_{58}$Cl$_2$N$_{14}$O$_4$S$_4$ [M$^{2+}$] m/z=546.1513, found 546.1523.

Example 4

[Chem. 32]

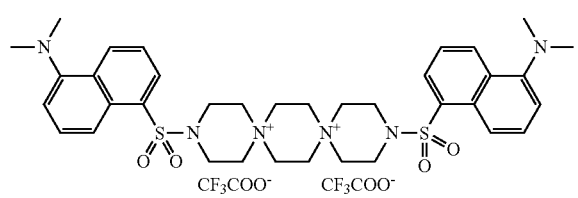

(5)

Compound (5) ditrifluoroacetate was synthesized by adding 100 µL of an aqueous solution of 3,12-diaza-6,9-diazoniadispiro-(5,2,5,2)-hexadecane dibromide (2.4 mg, 6.2 µmol) and 2.2 µL of triethylamine to dansyl chloride (3.6 mg, 13.5 µmol) dissolved in 250 µL of dioxane. After stirring at room temperature for 3 hours, 500 µL of acetone was added. The resulting white precipitate was washed with acetone and purified by reversed-phase HPLC (GL Sciences, Inc., Inertsil ODS-3, 4.6 mm×150 mm, flow rate 1.0 mL/min, 0.1% TFA MeOH/H$_2$O, 0→100%) to give Compound (5) ditrifluoroacetate as a white solid (3.6 mg, 82% yield).

$^1$H NMR (300 MHz, CD$_3$OD) δ 2.93 (s, 12H), 3.76-3.90 (m, 16H), 3.95-4.10 (m, 8H), 7.35 (d, J=8.0 Hz, 2H), 7.58 (d, J=8.0 Hz, 2H), 7.64 (t, J=7.7 Hz, 2H), 8.33 (d, J=7.7, 2H), 8.42 (d, J=7.7, 2H), 8.72 (d, J=8.0, 2H); FABMS (NBA) [M$^{2+}$] m/z=346; HRMS (FAB) calcd. for C$_{36}$H$_{48}$N$_6$O$_4$S$_2$ [M$^{2+}$] m/z=346.1589, found 346.1592.

Example 5

[Chem. 33]

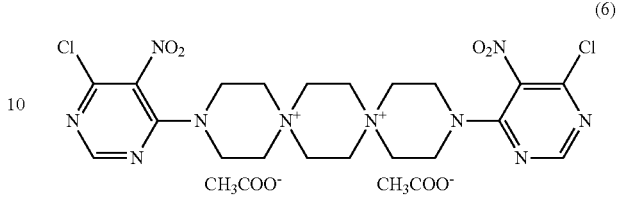

(6)

Compound (6) ditrifluoroacetate was synthesized by adding 100 µL of an aqueous solution of 3,12-diaza-6,9-diazoniadispiro-(5,2,5,2)-hexadecane dibromide (4.5 mg, 11.7 µmol) and 4 µL of triethylamine to 4,6-dichloro-5-nitropyrimidine (5 mg, 25.7 µmol) dissolved in 250 µL of dioxane. After stirring at room temperature for 3 hours, 500 µL of acetone were added. The resulting white precipitate was washed with acetone and purified by reversed-phase HPLC (GL Sciences, Inc., Inertsil ODS-3, 4.6 mm×150 mm, flow rate 1.0 mL/min, 0.1% TFA MeOH/H$_2$O, 0→100%) to give Compound (6) ditrifluoroacetate as a white solid (3.2 mg, 36% yield). $^1$H NMR (300 MHz, DMSO-d$_6$) 3.92-4.00 (m, 16H), 4.10-4.21 (m, 8H), 8.64 (s, 2H); FABMS (NBA) [M$^{2+}$] m/z=270.

Example 6

[Chem. 34]

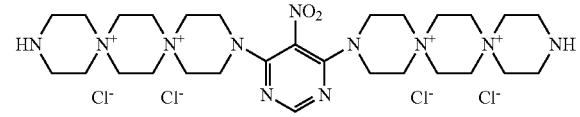

(7)

Compound (7) tetrachloride was synthesized by adding 100 µL of an aqueous solution of 3,12-diaza-6,9-diazoniadispiro-(5,2,5,2)-hexadecane dibromide (4.8 mg, 12.3 µmol) and 4 µL of triethylamine to 4,6-dichloro-5-nitropyrimidine (1.2 mg, 6.2 µmol) dissolved in 250 µL of dioxane. After stirring at room temperature for 30 minutes, the mixture was heated to 95° C. and stirred for an hour, and then 500 µL of acetone was added. The resulting white precipitate was washed with acetone to give Compound (7) tetrachloride as a white solid (3.8 mg, 85% yield). $^1$H NMR (300 MHz, D$_2$O) 3.07-3.19 (m, 8H), 3.51-3.65 (m, 8H), 3.72-4.20 (m, 40H); ESIMS (pos.) [M$^{4+}$] m/z=143.

Example 7

[Chem. 35]

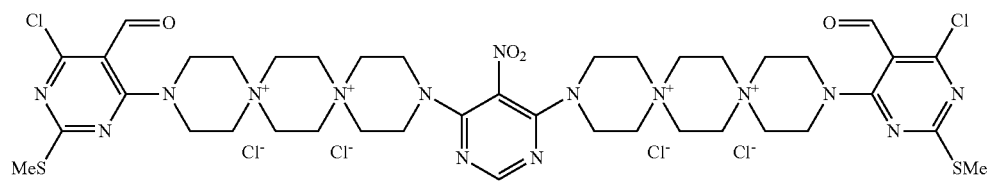

(8)

Compound (8) tetrachloride was synthesized by adding 50 μL of an aqueous solution of Compound (7) tetrachloride (0.9 mg, 1.3 μmol) and 1 μL of triethylamine to 4,6-dichloro-2-(methylthio)-5-formylpyrimidine (0.6 mg, 2.9 μmol) dissolved in 125 μL of dioxane. After stirring at room temperature for 3 hours, 500 μL of acetone was added. The resulting white precipitate was washed with acetone to give Compound (8) tetrachloride as a white solid (0.8 mg, 56% yield).

$^1$H NMR (300 MHz, D$_2$O) 2.42 (s, 6H), 3.75-4.20 (m, 48H), 8.02 (s, 1H), 10.00 (s, 2H); ESIMS (pos.) [M$^{4+}$] m/z=236.

Example 8

[Chem. 36]

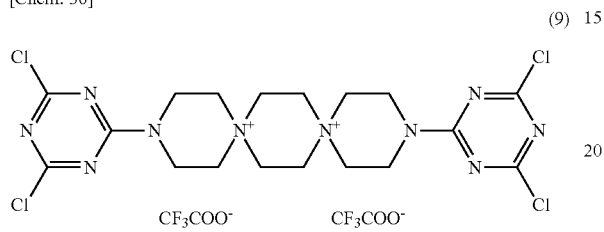
(9)

Compound (9) ditrifluoroacetate was synthesized by adding 200 μL of an aqueous solution of 3,12-diaza-6,9-diazoniadispiro-(5,2,5,2)-hexadecane ditrifluoroacetate (20 mg, 44 μmol) and 12 μL of triethylamine to cyanuric chloride (18.0 mg, 97 μmol) dissolved in 500 μL of ice-cooled dioxane. After stirring at 0° C. for 2 hours, 500 μL of acetone was added. The resulting white precipitate was washed with acetone to give Compound (9) ditrifluoroacetate as a white solid (25 mg, 77% yield).

$^1$H NMR (300 MHz, DMSO-d$_6$) 3.75-3.98 (m, 8H), 4.10-4.13 (m, 8H), 4.15-4.20 (m, 8H); ESIMS [M$^{2+}$] m/z=261.

Example 9

[Chem. 37]

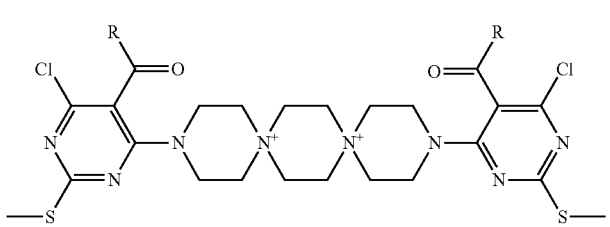
(10)

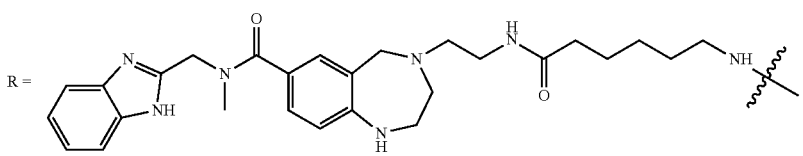

[Chem. 38]

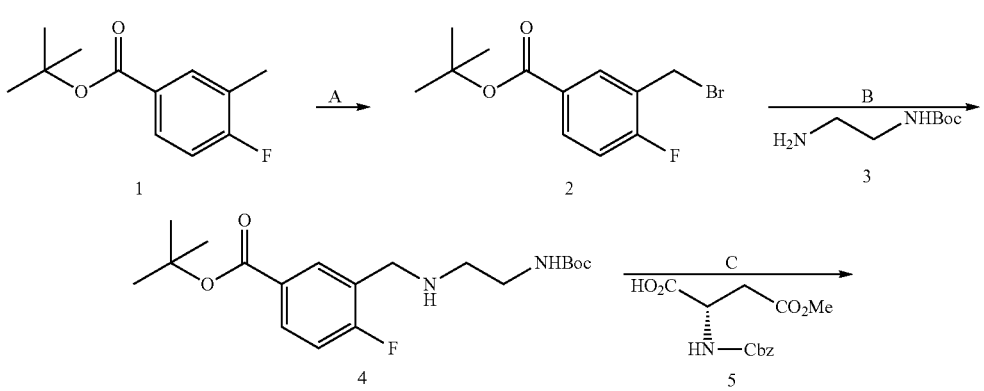

-continued
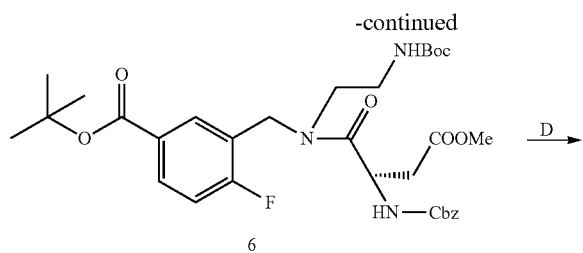
6
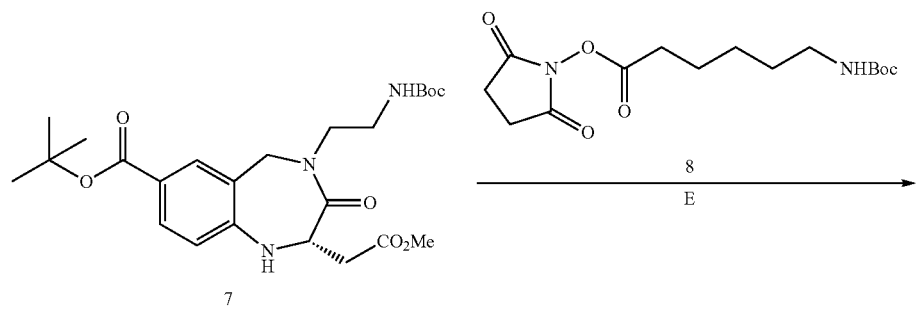
7    8
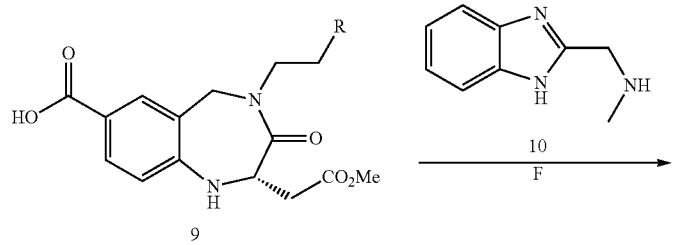
9    10
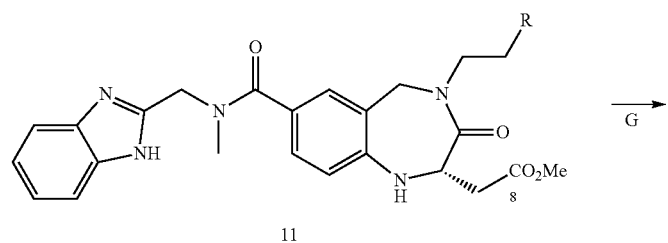
11
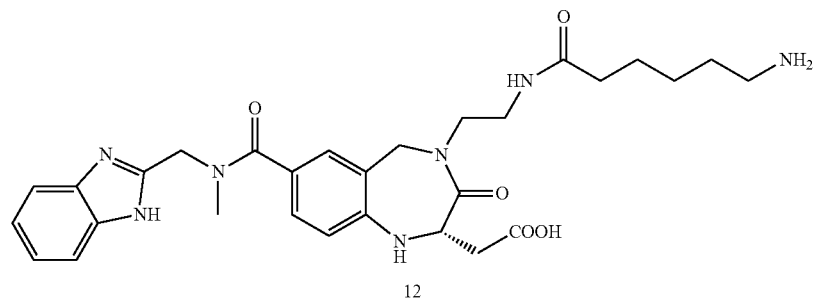
12
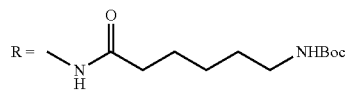

-continued

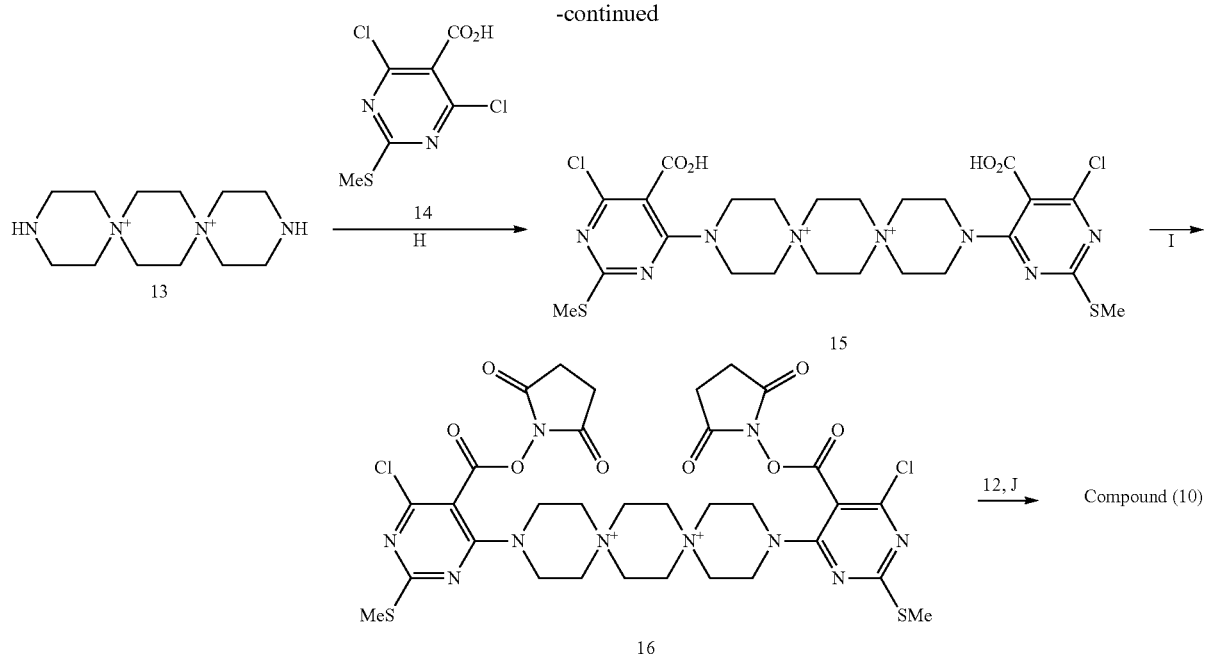

(A) NBS, AIBN, reflux; (B) DMF, room temperature; (C) EDC, HOBT, DMF; (D) (i) $H_2$ Pd—C (5%, w/w), MeOH, (ii) 0.01 M in DMSO, 130° C.; (E) (i) TFA, anisole, $CH_2Cl_2$, (ii) $iPr_2NEt$, DMF; (F) (i) EDC, HOBT, DMF; (G) 2M NaOH, MeOH-THF (1:1); (H) $Et_3N$, dioxane-$H_2O$, 80° C.; (I) DCC, N-hydroxysuccinimide, THF; (J) (i) TFA, anisole, $CH_2Cl_2$, (ii) $Et_2N$, $CH_3CN$, room temperature 1 (9.85 g) and N-bromosuccinimide (10 g) and AIBN (0.41 g) were refluxed in $CCl_4$ for 24 hours. The reaction mixture was filtered through a celite pad. The resulting solvent was condensed to give Crude Product 2.

3 (3 g) was added dropwise to 2 (5 g) dissolved in DMF. After stirring for 3 hours at room temperature, the solvent was condensed, and subjected to liquid-liquid distribution using water and ethyl acetate. The organic layer was condensed, and the resulting residue was purified by silica gel column chromatography to give 4 (304 mg). MS (ESI) 369 ($M^+$)

EDC (194 mg) and HOBT (145 mg) were added to DMF solution of 4 (304 mg) and 5 (264 mg). After stirring for 24 hours at room temperature, the solvent was subjected to liquid-liquid distribution using water and ethyl acetate. The organic layer was condensed, and the resulting residue was purified by silica gel column chromatography to give 6 (327 mg). MS (ESI) 654 ($MNa^+$)

Pd—C (5% w/w, 130 mg) was added to MeOH solution of 6 (327 mg), and the mixture was replaced by hydrogen and stirred for 24 hours. After filtrating the reaction mixture, the solvent was condensed, and the residue was purified by silica gel column chromatography to give a decarbobenzyl oxylation product (200 mg). The product was dissolved in DMSO anhydride and heated to 130° C. After stirring for 16 hours, the solution was subjected to liquid-liquid distribution using water and ether. The organic layer was condensed, and the resulting residue was purified by silica gel column chromatography to give 7 (60 mg). MS (ESI) 500 ($MNa^+$)

TFA was added to $CH_2Cl_2$ solution of 7 (60 mg). After stirring for 7 hours at room temperature, the solvent was condensed, and the crude product was dissolved in DMF. 8 (60 mg) and $iPr_2Net$ (0.2 mL) were added to the resulting liquid, followed by stirring for 4 hours at room temperature. The reaction mixture was subjected to liquid-liquid distribution using water and ethyl acetate. The organic layer was condensed, and the resulting residue was purified by silica gel column chromatography to give 9 (52 mg).

EDC (84 mg), HOBT (59 mg) and NMM (0.19 mL) were added to DMF solution of 10 (155 mg) and 9 (50 mg). After stirring for 3 hours, the solution was subjected to liquid-liquid distribution using water and ethyl acetate. The organic layer was condensed, and the resulting residue was purified by silica gel column chromatography to give 11 (104 mg).

NaOH (18 mg) dissolved in water (0.5 mL) was added to 11 (50 mg) dissolved in THF-MeOH (1:1, 2 mL). After stirring for 16 hours, 0.2 mL of acetic acid was added. The solvent was removed by condensation, and the resulting residue was purified by silica gel column chromatography to give 12 (32 mg). MS (ESI) 687 ($MNa^+$)

An aqueous solution of bromide salt of 13 (5 mg) was added to a dioxane solution of 14 (6.8 mg). After stirring for 15 minutes, 5 µL of triethylamine was added, followed by stirring for another 5 hours at 80° C. The reaction mixture was washed with acetone, and purified by reversed-phase HPLC to give 15 (4 mg). MS (ESI) 315 ($M^{2+}$)

A THF solution of 15 (2 mg), N-hydroxysuccinimide (1.2 mg), and DCC (2.3 mg) was stirred for 3 hours at room temperature. The solvent was removed by condensation.

12 (10 mg) was dissolved in $CH_2Cl_2$. TFA was added to remove Boc group. The solvent was condensed, and used directly for the next reaction. The deBoc product of 12 (1.6 mg) and 10 µL of triethylamine were added to an acetonitrile solution of the resulting crude product 16 (1.2 mg). After stirring for 14 hours at 0° C., the solvent was removed by condensation. The resulting residue was purified by reversed-phase HPLC to give a compound (10) (2.4 mg). MS (ESI) 788 ($M^{2+}$)

Materials 3,12-diaza-6,9-diazoniadispiro-(5,2,5,2)-hexadecane dibromide (compound 3) was purchased from Sigma-Aldrich. 4,6-dichloro-5-nitropyrimidine, dansyl chloride, cyanuric chloride, and sodium tetrahydroborate were purchased from Wako Pure Chemical Industries, Ltd. 4,6-dichloro-2-(methylthio)-5-formylpyrimidine was purchased from Toronto Research Chemicals. Dansyl hydrazine was purchased from Tokyo Kasei Kogyo Co., Ltd. Compounds 1 3, 4 and 5 were produced according to the above method. Adhesamine and its derivatives (2-5) were diluted by DMSO to its working concentrations before being subjected to cell-adhesion assays and ITC experiments. Type I collagen from salmon skin and fibronectin from bovine plasma (Wako Pure Chemical Industries, Ltd.), poly-L-lysine hydrochloride (Peptide Institute. Inc.), and poly-L-ornithine hydrobromide (MP Biomedicals, Inc.) were dissolved in Milli-Q water and stored at −20° C. until required for use. Heparin (average molecular mass (Mw), 18.0 kDa) and heparan sulfate (Mw, 13.6 kDa) were purchased as sodium salts from MP Biomedicals Inc. and Celsus, respectively. Chondroitin sulfate A (Mw, 37.5 kDa), keratan sulfate (Mw, 30.0 kDa), and hyaluronic acid (Mw, 125.0 kDa) were obtained from Seikagaku Corporation. Rabbit anti-FAK (C-20) antibody and rabbit anti-ERK (C-16) antibody were purchased from Santa Cruz Biotechnology. Mouse anti-FAK (phospho-tyrosine 397) antibody was obtained from BD Biosciences PhaLmingen. Rabbit anti-ERK1/2 phospho-threonine$^{202}$/tyrosine$^{204}$ (pERK) antibody was purchased from Cell Signaling Technology. Anti-rabbit and anti-mouse immunoglobulin G (IgG) (horseradish peroxidase-linked, whole antibody) and ECL Plus Western blotting detection reagents were purchased from GE Healthcare. Synthetic RGD-specific peptide (GRGDTP) was obtained from Sigma-Aldrich.

Cell Culture and Small Molecule Screen

HepG2 cells were cultured in MEM supplemented with 10% fetal bovine serum (FBS) and 1% penicillin/streptomycin at 37° C. under 5% $CO_2$. Jurkat cells were cultured in RPMI-1640 supplemented with 10% fetal bovine serum (FBS) and 1% penicillin/streptomycin at 37° C. under 5% $CO_2$. For the screening of small molecule compounds, 100 μL of HepG2 suspension ($2\times10^5$ cells/mL) was plated into 96-well plates supplied with each compound at a concentration of 20 μg/mL. After 3, 16, and 24 hours, the cells were subjected to microscopic observation to examine phenotypic changes. CHO K1 cells and CHO mutant cell lines were maintained in Ham's F-12 medium supplemented with 7.5% fetal bovine serum.

Cell Adhesion Assay

Assay by Addition

1 μL each of an aqueous solution of adhesamine (1), Type I collagen, poly-L-lysine hydrochloride, poly-L-ornithine hydrobromide, and fibronectin at a concentration of 50, 500, and 5000 μg/ml, was added to 96-well plate. 100 μL of HepG2 suspension ($4\times10^5$ cells/mL) was added to each well. After 3-hour incubation at 37° C., non-adherent cells were removed by washing each well with PBS three times, and the attached cells were counted with a Neubauer counting chamber (Digital Bio). For Jurkat cells, 100 μL of cell suspension was added to each well at a density of $1\times10^6$ cells/ml. After 5-hour incubation at 37° C., non-adhered cells were removed by washing each well with PBS twice, and the attached cells were counted with a Neubauer counting chamber (Digital Bio). To calculate adhesion rates, firstly seeded cell numbers were assigned a value of 100%. As control tests, the same tests were conducted using wells supplied with only 1 μL of DMSO. Each assay was conducted in triplicate, and the means and standard derivations were calculated.

For CHO wild-type and CHO mutant cell lines, 100 μL of trypsinized cell suspension in a culture medium was added to each well at a density of $2\times10^5$ cells/mL. After 5-hour incubation at 37° C., non-adhered cells were removed by washing each well with PBS twice, and the attached cells were counted with a Neubauer counting chamber (Digital Bio). To calculate adhesion rates, the cell numbers before washing were assigned a value of 100%. Each assay was conducted in triplicate, and the means and standard derivations were calculated for a minimum of three independent experiments.

Assay by Coating

The assay samples (adhesamine (1), Type I collagen, poly-L-lysine hydrochloride, poly-L-ornithine hydrobromide, and fibronectin) were adjusted in concentration by being diluted with 10 mM PBS containing 1% DMSO. 100 μL of each solution (1, 10, and 100 μg/mL) was added to 96-well plates and incubated overnight at 4° C. Thereafter, the wells were washed with Milli-Q water twice. 100 μL of Jurkat cell suspension ($1\times10^6$ cells/mL) was added to each of coated wells. After 5-hour incubation at 37° C., non-adhered cells were removed by washing each well with PBS twice, and attached cells were counted with a Neubauer counting chamber (Digital Bio).

The comparison between adhesamine and its derivatives regarding cell adhesion promotion activity was conducted using Jurkat cells by way of reagent addition assay. 1 μL each of DMSO solutions of the compounds having concentrations of 60, 600, and 6000 μM were added to 96-well plates. The wells were supplied with 100 μL each of Jurkat cell suspensions ($1\times10^6$ cells/mL). After 5-hour incubation at 37° C., non-adhered cells were removed by washing each well with PBS twice, and the attached cells were counted with a Neubauer counting chamber (Digital Bio). To calculate adhesion rates, firstly seeded cell numbers were assigned a value of 100%. As control tests, the same tests were conducted using well plates supplied with only 1 μL of DMSO. Each assay was conducted in triplicate, and the means and standard derivations were calculated.

Squelching Assay

Adhesamine (1: 0.6 nmol) and each glycosaminoglycan (GAG) (heparin, heparan sulfate, chondroitin sulfate, keratan sulfate, hyaluronic acid, and heparin oligosaccharides) ranging from 0.006 to 12 nmol were stirred in 10 μL of 50 mM phosphate buffer (pH 6.0) containing 100 mM NaCl and 1% DMSO with a vortex mixer at room temperature for 30 min. Thereafter, these mixtures were transferred to 96-well plates, and 90 μL of Jurkat cell suspension ($1\times10^5$ cells/mL) was added to each well. After 5-hour incubation at 37° C., non-adherent cells were removed by washing each well with PBS twice, and the attached cells were counted with a Neubauer counting chamber (Digital Bio). To calculate the inhibition rates, the number of attached cells in the wells supplied only with 1% DMSO or GAG of each concentration was subtracted from the number of cells in which the cell adhesions were observed after addition of the samples. The inhibition rate is expressed as follows.

$$\left(1 - \frac{AC_{+GAGs, +adhesamine} - AC_{+GAGs, -adhesamine}}{AC_{-GAGs, +adhesamine} - AC_{-GAGs, -adhesamine}}\right) \times 100 \qquad \text{[Math. 1]}$$

wherein $AC_{+(-)GAGs, +(-)adhesamine}$ expresses the number of adhered cells in the presence (absence) of GAGs and adhesamine.

$IC_{50}$ values are defined as the concentrations of GAGs required for 50% inhibition of the adhesamine (6 μM)-induced cell attachment. The results of the squelching assays were plotted as percentage of inhibition vs. log (GAG), and $IC_{50}$ values were determined from curve fits of multiple independent experiments.

Isothermal Titration Calorimetry (ITC)

ITC experiments were performed at 25° C. using a MicroCal VP-ITC microcalorimeter. 10 µL of adhesamine (15 µM) was titrated with 25×10 µL injections of GAGs (2.7 mM of heparan sulfate, heparin, chondroitin sulfate, hyaluronic acid and heparin oligosaccharides). The titrations were carried out in 50 mM phosphate buffer (pH 6.0) containing 100 mM NaCl and 1% DMSO. Since the molecular weights of GAGs vary depending on the polymerization degrees, it is necessary to correct the difference before comparing the thermal flows in the ITC. Therefore, the mole concentrations of GAGs are given as the concentrations of their disaccharide units.

Cell Detachment Assay

1 µL DMSO solution of adhesamine (1) (6 mM) was dispensed to each well on a 96-well plate. Jurkat cells were suspended in the growth medium, and 100 µL of cell suspension was added to each well at a density of $1 \times 10^6$ cells/mL. After 5-hour incubation at 37° C., the medium was aspirated, and the plates were washed twice with PBS. 100 µL of fresh medium was added to each well. After further 4, 8, 14 and 24-hour incubation at 37° C., non-adhered cells were removed by washing with PBS twice, and the attached cells were counted with a Neubauer counting chamber. To calculate adhesion rates, the cell numbers before washing were assigned a value of 100%. Each assay was conducted in triplicate, and the means and standard derivations were calculated for a minimum of three independent experiments.

Confocal Imaging

HepG2 cell suspension (100 µL) were seeded on a 96-well plate (Greiner bio-one) at a density of $2 \times 10^5$ cells/mL, and the cells were incubated with Compounds 4 and 5 for 3 hours at 37° C., at a concentration of 6 µM. After incubation, medium exchange was performed, and the cells were then subjected to fluorescent microscopic observation. Microscopic images of the cells were captured by a Yokogawa CSU22 confocal fluorescence microscope with 405 nm laser excitation.

Enzymatic Treatment of Cells

Jurkat cells ($5 \times 10^4$) were cultured in 100 µL of RPMI and treated with a combination of heparinase, heparitinase I, and heparitinase II (0.02 units/mL) or chondroitinase ABC (0.1 units/mL) for 30 min at room temperature. The ability of the treated cells to respond to adhesamine was evaluated by counting the cells that were attached to plastic wells of a 96-well plate in the presence of adhesamine (6 µM).

Cell Growth Assay

1 µL DMSO solution of adhesamine (1) was added to 96-well plate at a concentration of 600 µM. HepG2 cells and Jurkat cells were suspended in the growth medium, and 100 µL of cell suspension was added to each well at a density of $2 \times 10^5$ and $4 \times 10^5$ cells/mL, respectively. After incubation for indicated time, the cell viability was measured using Cell Counting Kit-8 (Dojindo Molecular Technologies, Inc., Gaithersburg, Md.), which contains a tetrazolium salt (WST-8) that produces a water-soluble formazan dye by NADH dehydrogenases in living cells. 5 µl of WST-8 assay solution was added to 100 µl of the growth medium per well, and incubated for 4 hours. The optical density (OD) of the solution was read by a microplate reader, using a test wavelength at 450 nm and a reference wavelength at 650 nm. The cell viability incubated in the growth medium containing 1% (v/v) of DMSO was assigned a value of 100%. Each assay was conducted in triplicate, and the means and standard derivations were calculated for a minimum of three independent experiments.

Visualization of Actin Cytoskeleton with Rhodamine-Conjugated Phalloidin

Jurkat or HepG2 cells were plated onto glass coverslips in the presence of adhesamine (6 µM). They were fixed after 5 or 3 hours, respectively, with 4% paraformaldehyde for 20 minutes. The cell membrane was permeabilized by 5-min treatment with 0.1% Triton X-100 (in PBS). Samples were washed twice with PBS, and actin cytoskeleton was visualized with rhodamine-conjugated phalloidin according to the manufacturer's instructions (Invitrogen). The cell images were captured with a Yokogawa CSU22 confocal fluorescence microscope with 588-nm laser excitation.

Cytoskeletal Disruption

Jurkat cells ($5 \times 10^4$) were cultured in 100 µL of RPMI, and incubated with cytochalasin B (0-100 µM) or nocodazole (0-0.5 µM) at 37° C. The treated cells were then assayed for their responses to adhesamine (6 µM). Their responses to fibronectin- or poly-L-lysine-coated plates were also evaluated. The coated plates were prepared by pretreating wells of 96-well plates with fibronectin or poly-L-lysine (1 ng/well).

Western Blotting

Jurkat cells were maintained in an RPMI medium containing 10% FBS. 5-6 million Jurkat cells were dispensed to a well of a 6-well plate in a final volume of 2 mL, and then incubated at 37° C. for 0-5 hours in the presence of adhesamine or poly-L-lysine. Non-adherent cells were removed and pelleted, and the remaining adherent cells were lysed in a 125 mM Tris-HCl buffer (pH 6.8) containing 4% SDS, 10% glycerol, 0.006% bromophenol blue, and 1.8% β-mercaptoethanol. The adherent cell homogenate was combined with pelleted nonadherent cells from the same well, and the combined sample was boiled for 5 minutes. The samples were separated by SDS-PAGE and electroblotted onto a nitrocellulose membrane. The membranes were blocked in 1% BSA and incubated with primary antibody, and then with horseradish peroxidase-conjugated secondary antibody. The blots were developed using the enhanced chemiluminescence technique.

Microinjection

The solutions of adhesamine (1), Type I collagen, poly-L-lysine hydrochloride, and fibronectin were prepared by diluting with PBS containing 1% (v/v) DMSO. 10 µL of each solution (1 mg/mL) was added to glass bottom culture dishes (35 mm uncoated dish). 2 mL of cell suspension in a culture medium was added to each well at a density of $2 \times 10^5$ cells/mL. After 14-hour incubation at 37° C., Alexa Fluor 594 (Molecular Probes, USA) at a concentration of 5 mg/mL was injected into Jurkat cells by using a CI-2000 automated cell injection system (Fujitsu, Japan). Success rates of the microinjection were evaluated by direct observation of the fluorescent cells through a fluorescent-microscopic window of the injection system. The data shown are means±SD for a minimum of three experiments. 20 cells were injected in each experiment.

Test Example 1

It was observed that HepG2 cells attach more strongly to culture plates in the presence of adhesamine (FIGS. 1A, B). To confirm that the molecule promotes cell adhesion, the HepG2 cells were desorbed from the plate by trypsin treatment, and were cultured in the presence of 0.6-60 µM adhesamine to examine reattachment of the cells to a culture plate. A 3-hour incubation time was used, because HepG2 cells began to attach to the culture plate within 3 hours. After 3 hours, the plates were washed with phosphate buffer to remove unattached cells, and adhered cells remaining on the plate were counted. The results[1] showed that adhesamine enhances the adhesion of HepG2 cells up to twofold, and that the effect is concentration-dependent (FIG. 1C).

Figure 2:
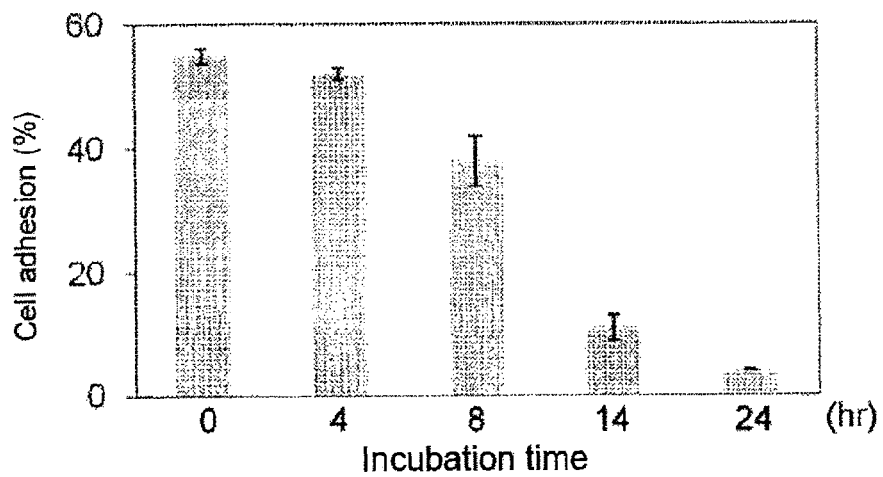
FIG. 2 is a graph illustrating a reversible activity of adhesamine (1). The attached cells were counted at the indicated time points after removal of adhesamine (1). In order to calculate adhesion rates, the number of cells before washing was assigned a value of 100%. Each assay was conducted in triplicate, and the means and the standard deviations were calculated for a minimum of three independent experiments.

However, since HepG2 cells have an intrinsic propensity to adhere to plastic tissue-culture plates, a test was conducted to determine whether the same effect was also obtained in the Jurkat cell line and human T-lymphocytes that are floating cells. Remarkably, 30% and 60% of the Jurkat cells attached to a culture plate in the presence of 6 and 60 μM of adhesamine, respectively (FIG. 1D). Removal of adhesamine by washing the plate twice with PBS detached the cells. 93% of Jurkat cells were released from the surface of a culture plate 24 hour after washing (FIG. 2). The results indicate that the effect of adhesamine is reversible. It is noteworthy that adhesamine did not induce cell-cell adhesion, but enhanced adhesion of cells and substrates. Simply adding adhesamine to the medium promoted adhesion of Jurkat cells onto culture plates, but not to each other.

Test Example 2

Figure 3:
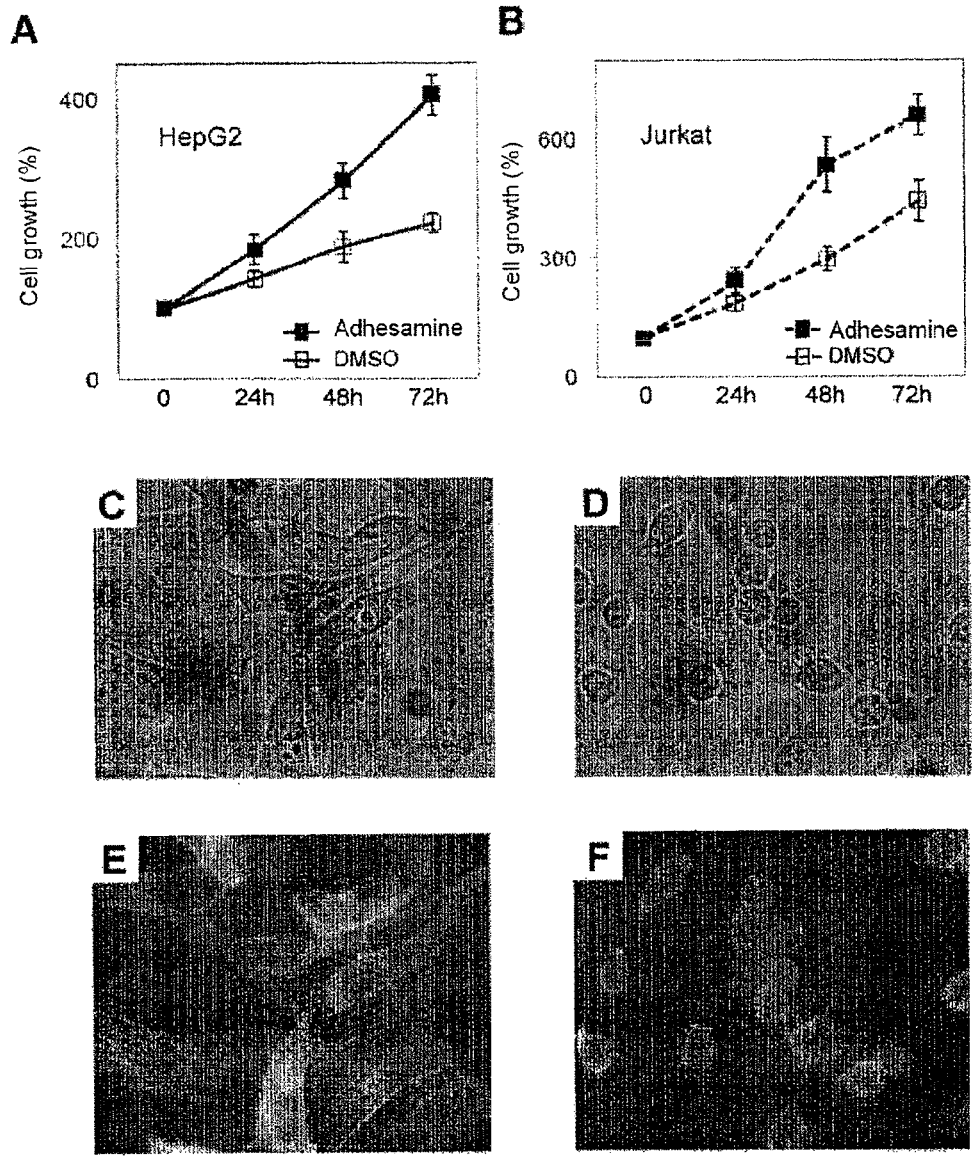
FIG. 3 shows effects of adhesamine (1) on the cell growth and cytoskeletal networks. In (A) and (B), the cell growth was determined at 24, 48, and 72 hours after the addition of adhesamine (1) (6 μM). The cell growth in the presence of 1% (v/v) DMSO was assigned a value of 100%. The data shown are means±SD for a minimum of three experiments. (C) to (F) show the rearrangement of actin filaments in HepG2 and Jurkat cells in the presence of adhesamine (6 μM). Brightfield images (C and D) and confocal images (E and F) are shown. HepG2 (C and E) or Jurkat (D and F) cells were plated for 5 hours or 3 hours, respectively, and actin cytoskeletal was visualized using rhodamine-labeled phalloidin.

Adhesamine had no obvious cytotoxicity in the tested cell lines. The growth of the cells was actually slightly enhanced (FIG. 3AB), and the cell morphology appeared normal, as in the manner of well-maintained HepG2 and Jurkat cells (FIG. 1). Visualization of actin cytoskeletons with rhodamine-conjugated phalloidin revealed the F-actin networks in adhered cells. Actin filament bundles ran in parallel to the cell axis or through cell processes in HepG2 cells, and a well-organized cortical actin structure, which is reminiscent of the survival phenotype, formed in Jurkat cells (FIG. 3EF). Such organized actin structures were not detected in the cells attached to a plate coated with poly-L-lysine, a non-specific coating reagent.

Figure 4:
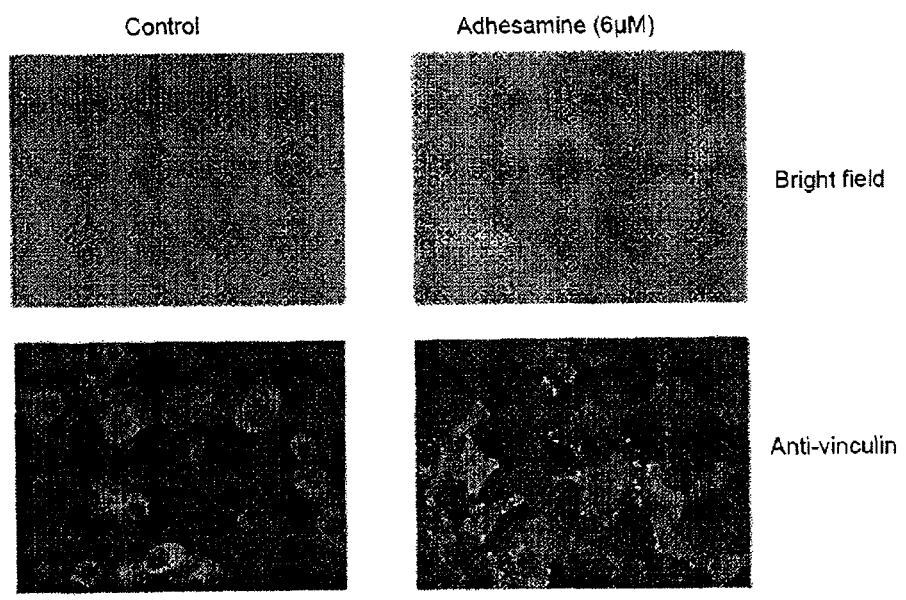
FIG. 4 shows focal adhesion formation by adhesamine. Trypsin-treated HepG2 cells were plated for 3 hours onto coverslips to which adhesamine was added; fixed thereon; and stained with anti-vinculin antibody and Alexa Fluor 488 goat anti-mouse IgG.

The cells were also stained with an antibody against vinculin, a marker of focal adhesion. Vinculin-containing focal adhesions were observed in adhesamine-treated cells immediately after seeding, when non-treated HepG2 cells had not yet formed contacts (FIG. 4). These observations indicate that the adhesamine-induced contacts of the cells to the plates initiate a normal schedule of cell adhesion[2,3].

Figure 5:
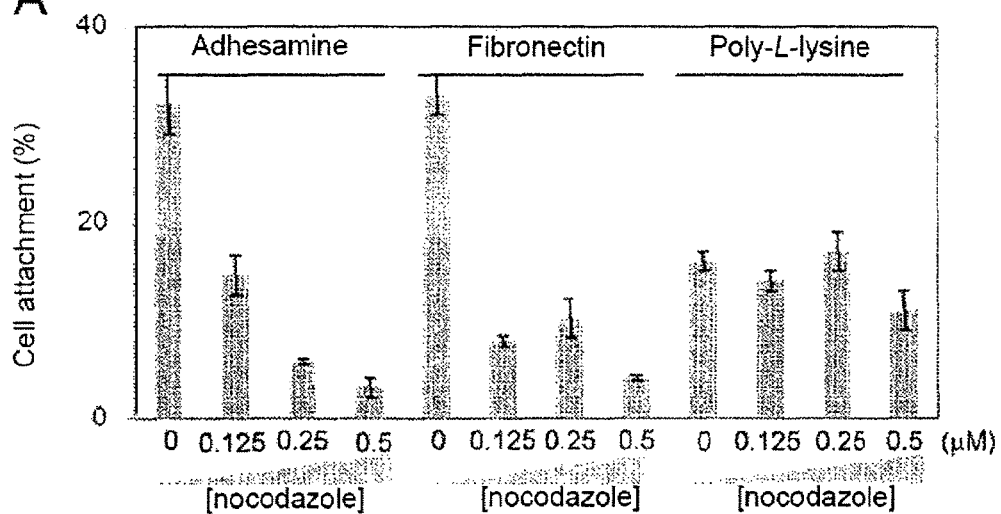
FIG. 5 shows graphs illustrating effects of a cytoskeletal inhibitor on adhesamine-induced cell adhesion. Jurkat cells were adhered to plastic plates by adding adhesamine thereto in the presence of nocodazole (a tubulin inhibitor) or cytochalasin B (an actin inhibitor). Both nocodazole and cytochalasin inhibited adhesamine-induced cell adhesion, as observed in the cells adhered to a fibronectin-coated plate. The cell adhesion to poly-L-lysine-coated plates was hardly inhibited by cytochalasin B and nocodazole. The concentration of adhesamine was 6 μM. The fibronectin- or poly-L-lysine-coated plates were prepared by pretreating wells of 96-well plates with fibronectin or poly-L-lysine (1 ng/well).
Figure 5:
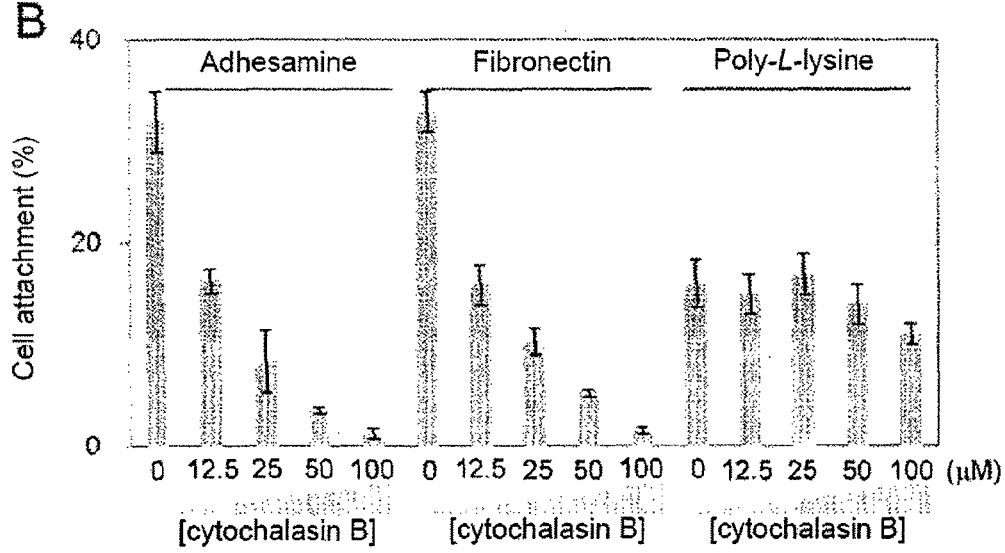

To examine the adhesamine-mediated adhesion, the effects of cytoskeletal disruption were evaluated. Adhesion assays were performed after treatment with cytochalasin B or nocodazole, drugs that disrupt formation of actin filaments and microtubules, respectively[4,5]. Both cytochalasin B and nocodazole inhibited the adhesamine-mediated cell adhesion in a dose-response manner, just as they impaired the fibronectin-mediated cell adhesion. In contrast, the two reagents had no detectable effects on the cell attachment induced by poly-L-lysine (FIG. 5AB). These data collectively suggest that adhesamine induces cell adhesion similar to that induced by native extracellular matrix.

Test Example 3

Figure 6:
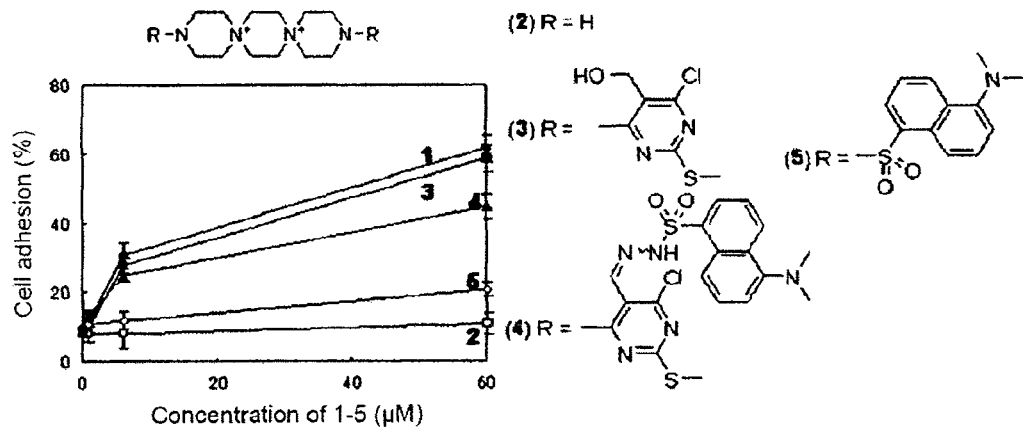
FIG. 6 shows a graph illustrating chemical structures and cell-adhesion of derivatives of adhesamine (1). Their ability to promote cell adhesion was evaluated with Jurkat cells.

To analyze the mechanism of the adhesamine-induced cell adhesion, at first, the activities of two adhesamine derivatives were evaluated. The results showed that removal of terminal pyrimidine rings completely eliminated the activity (FIG. 6, Compound 2); however, it also showed that reduction of the aldehyde groups in the pyrimidine rings to hydroxyl groups had no impact on activity (Compound 3). Therefore, behaviors of the molecules were then examined by introducing a fluorescent group into the aldehyde parts on the pyrimidine rings. Dansyl group was used as the fluorescent group. The produced dansyl conjugate of adhesamine (Compound 4) maintained the cell-adhesion promoting activity.

Figure 7:
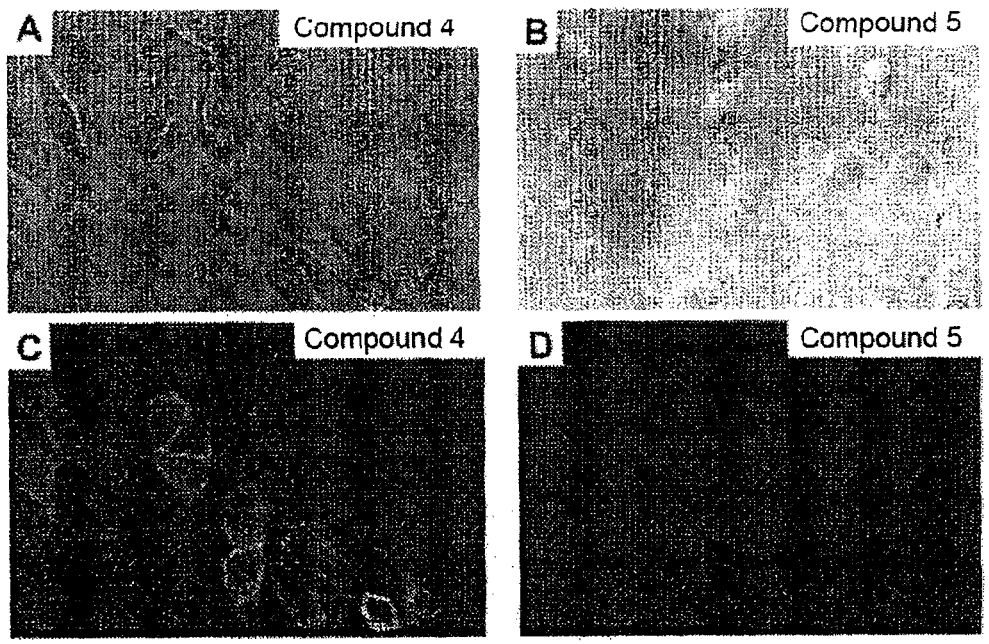
FIG. 7 shows micrographs of brightfield (A and B) and confocal (C and D) images. HepG2 cells were incubated with Compound 4 (6 μM, A and C) or Compound 5 (6 μM, B and D) for 3 hours after seeding.

Fluorescence microscopic observation of Compound 4 revealed the localization of the fluorescent probe (Compound 4) on the cell surface (FIGS. 7A, 7C). In contrast, a dansyl conjugate of dispirotripiperazine (5), which exhibited little effect on cell adhesion, showed no clear localization (FIGS. 7B, 7D).

Figure 8:
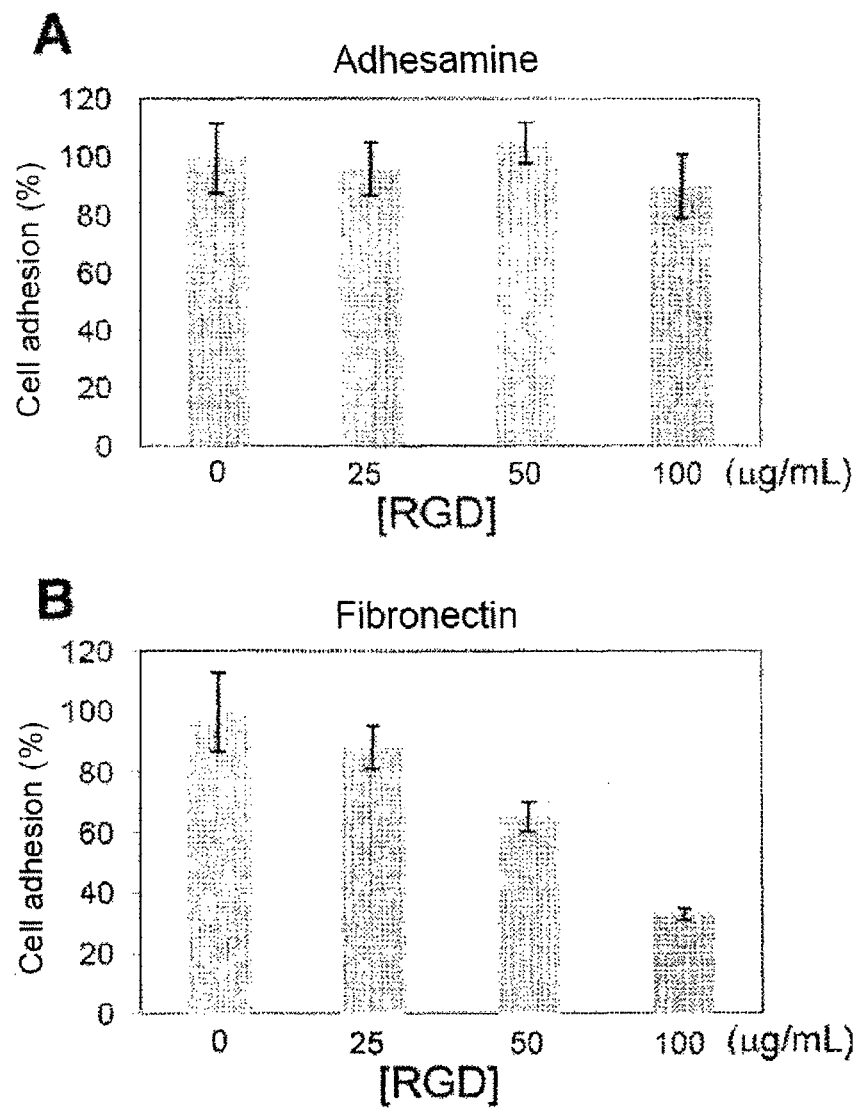
FIG. 8 shows effects of an RGD peptide on adhesamine-induced cell adhesion. In (A) and (B), Jurkat cells were seeded onto adhesamine-added or fibronectin-coated plastic plates in the presence of increasing amounts of an RGD peptide (0-100 μg/mL). The concentrations of adhesamine and fibronectin were 6 μM and 5 μg/mL, respectively. The attached cells were counted at 5 hours after seeding. Each point represents the means±SD.

Candidates of the cell-surface targets were integrins, well-known cell-surface receptors for an extracellular matrix such as fibronectin. To explore the possibility, an Arg-Gly-Asp (RGD) peptide, which binds to and masks the fibronectin-interacting domain of integrins, was added to the medium, and its ability to squelch the activity of adhesamine was examined. The RGD peptide reduced attachment of Jurkat cells on a fibronectin-coated plate, but failed to inhibit the adhesamine-induced attachment of Jurkat cells, even at a high concentration (100 μg/mL) (FIGS. 8A, 8B). It is unlikely that adhesamine exerts its activity through interacting with the fibronectin-recognition domain of integrins.

Other potential targets of adhesamine are glycosaminoglycans (GAGs)[6], negatively charged cell-surface glycans that have been reported to play an important role in cell adhesion together with integrins[7]-[11]. GAGs are classified into five kinds—heparin, heparan sulfate, chondroitin sulfate, keratan sulfate, and hyaluronic acid. Each GAG was added to the medium together with adhesamine, and their ability to squelch the activity of adhesamine was examined (Table 1). The results show that heparin, heparan sulfate, and keratan sulfate decreased the activity of adhesamine, with $IC_{50}$ values of 0.27, 0.79 and 1.03 μM, respectively ($IC_{50}$ values are defined as the concentrations of oligosaccharides required for 50% inhibition of the adhesamine (6 μM)-induced cell attachment). Chondroitin sulfate and hyaluronic acid had no detectable effect. To confirm the interactions between adhesamine and the molecules, the heat quantity induced by the binding of adhesamine to each GAG was measured by way of ITC[12]. Clear exothermic interactions were observed for heparin, heparan sulfate, and keratan sulfate with $K_D$ values of 0.39, 4.67, and 5.85 μM, respectively. Titrations with chondroitin sulfate and hyaluronic acid failed to display signals strong enough for $K_D$ estimation. These data suggest that adhesamine interacts selectively with heparin, heparan sulfate, and keratan sulfate on the cell surface.

TABLE 1

Results of ITC measurements and squelching assays with GAGs[a]

| GAGs | $K_d$(μM) | n (no. of adhesamine per GAGs) | $IC_{50}$[b](μM) |
|---|---|---|---|
| Heparin | 0.39 ± 0.09 | 20.34 ± 2.53 | 0.27 ± 0.05 |
| Heparan sulfate | 4.67 ± 0.49 | 6.38 ± 0.49 | 0.79 ± 0.19 |
| Keratan sulfate | 5.85 ± 4.75 | 33.28 ± 3.2 | 1.03 ± 0.11 |
| Chondroithin sulfate | n.d.[c] | — | >120 |
| Hyaluronic acid | n.d.[c] | — | >120 |

[a]All data were collected in 50 mM phosphate buffer (pH 6.0) containing 100 mM NaCl and 1% DMSO at 25° C.
[b]$IC_{50}$ values are defined as the concentrations of GAGs required for 50% inhibition of the adhesamine (6 μM)-induced cell attachment.
[c]Not determined due to insufficient heat release.

For detailed analyses of the interaction, we focused on heparin with the highest $K_D$ as a model. Heparin is a linear polysaccharide essentially comprised of repeating disaccharide units (sulfated uronic acid-D-glucosamine)[13]. To define a minimal binding unit, interactions of adhesamine with heparin oligosaccharides of various sizes (disaccharide, tetrasaccharide, hexasaccharide, octasaccharide, and decasaccharide) were examined by both squelching assays and ITC. In both experiments, the hexasaccharide displayed the highest affinity for adhesamine (Table 2). ITC results also revealed that two molecules of adhesamine bind to a hexasaccharide unit of heparin with a $K_D$ value of 0.12 μM.

TABLE 2

Results of ITC measurements and squelching assays with heparin oligosaccharides[a]

| heparin oligosaccharides | $K_c$ (μM) | n (no. of adhesamine per oligosaccharides) | $IC_{50}$[b](μM) |
|---|---|---|---|
| Disaccharide | n.d.[c] | — | >120 |
| Tetrasaccharide | n.d.[c] | — | >120 |
| Hexasaccharide | 0.12 ± 0.03 | 2.16 ± 0.43 | 2.09 ± 0.13 |
| Octasaccharide | 0.45 ± 0.14 | 2.29 ± 0.17 | 2.18 ± 0.29 |
| Decasaccharide | 2.09 ± 0.14 | 3.42 ± 0.72 | 2.3 ± 0.26 |
| Polysaccharide (54 mer) | 0.39 ± 0.09 | 20.34 ± 2.53 | 0.27 ± 0.05 |

[a]All data were collected in 50 mM phosphate buffer containing 100 mM NaCl and 1% (v/v) DMSO at 25° C.
[b]$IC_{50}$ values are defined as the concentrations of oligosaccharides required for 50% inhibition of the adhesamine (6 μM)-induced cell attachment.
[c]Not determined due to insufficient heat release.

Test Example 4

The cell adhesion promotion activities of other adhesamine derivatives were evaluated. Table 3 shows the results.

TABLE 3

| Compound Number | Jurkat cell adhesion rate (%) in 6 μM of Adhesamine |
|---|---|
| 6 | 22 ± 3.2 |
| 7 | 21 ± 1.3 |
| 8 | 28 ± 4.1 |
| 9 | 35 ± 5.2 |

Test Example 5

Figure 9:
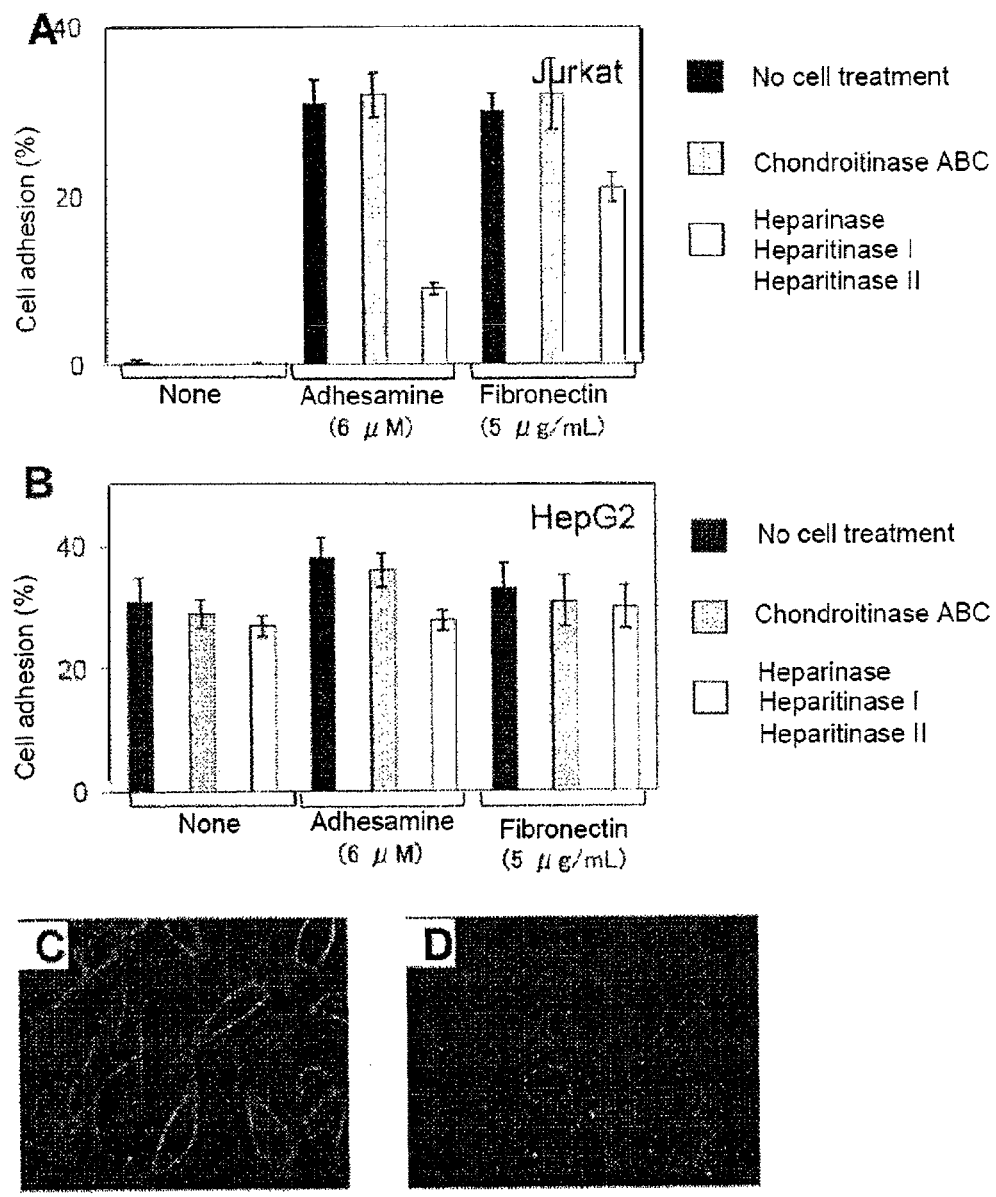
FIG. 9 shows effects of heparan sulfate digestive enzymes on adhesamine-induced cell adhesion. In (A) and (B), Jurkat cells (A) or HepG2 cells (B) were pretreated with 0.02 units/mL of heparinase, heparitinase I, and heparitinase II, or 0.1 units/mL of protease-free chondroitinase ABC in a serum-free culture medium for 1 hour at 37° C. before evaluating cell adhesion. The treated cells were seeded onto adhesamine-added or fibronectin-coated plastic wells. The attached cells were counted at 5 hours after seeding. The concentrations of adhesamine and fibronectin were 6 μM and 5 μg/mL, respectively. Each point represents the means±SD. (C) and (D) show localization of Compound 4 in HepG2 cells treated with heparinase/heparitinase I/heparitinase II (C) or chondroitinase ABC (D).

To confirm that cell adhesion with adhesamine is mediated by cell-surface heparan sulfate, Jurkat cells were treated with GAG-degrading enzymes. Degradation of cell-surface heparan sulfate chains with heparinase, heparitinase I, and heparitinase II (0.02 units/mL) reduced the adhesamine-induced cell attachment. In contrast, a five-fold greater concentration (0.1 units/mL) of chondroitinase ABC had no detectable effects on the adhesamine-induced cell adhesion (FIG. 9A). Digestion of heparan sulfate also affected the attachment of cells to fibronectin-coated plates, although the influence was less than that for adhesamine-treated cells (FIG. 9A). This is consistent with the previous finding that fibronectin binds both integrins and heparan sulfate to mediate cell adhesion.

The effects of these GAG-degrading enzymes on the intact or adhesamine-enhanced attachment of HepG2 cells were examined. The intact attachment of HepG2 cells was slightly impaired by treatment with GAGs-degrading enzymes: 13% and 7% inhibition were observed when cells were treated with heparinase/heparitinase I/heparitinase II (0.02 units/mL) or chondroitinase ABC (0.1 units/mL), respectively (FIG. 9B). As observed in Jurkat cells, adhesamine-induced cell adhesion was canceled by heparan sulfate-degrading enzymes, but not by chondroitinase ABC (FIG. 9B).

The effects of the GAG-degrading enzymes on localization of the fluorescent probe of Compound 4 were investigated. When cells were treated with heparan sulfate-degrading enzymes, Compound 4 was diffused from the cell surface, while chondroitinase treatment exhibited no impact on the cell-surface localization of Compound 4 (FIG. 9CD). These results support the notion that adhesamine induces cell adhesion through its interaction with cell-surface heparan sulfate.

Figure 10:
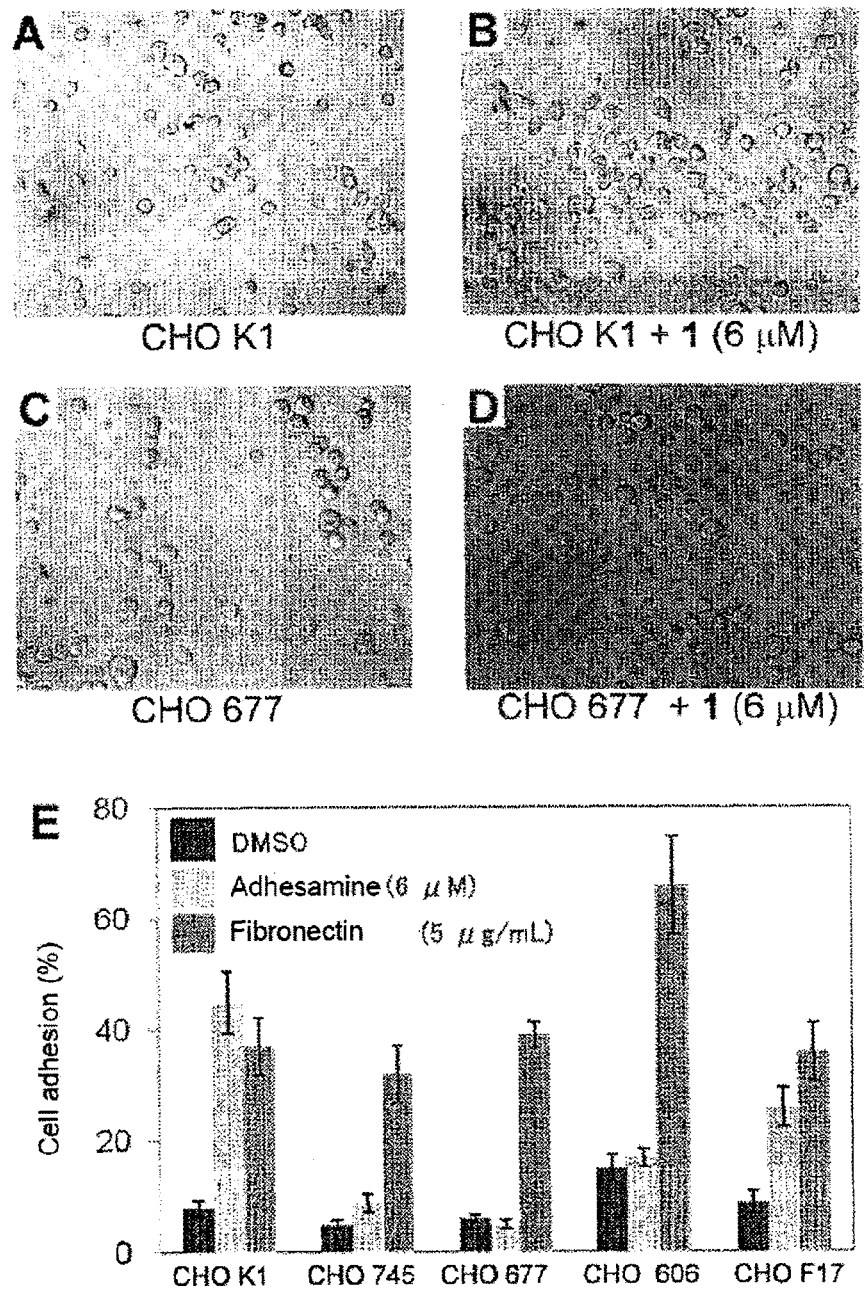
FIG. 10 shows effects of adhesamine on CHO-K1 and glycosaminoglycan-deficient mutants. (A) and (B) show CHO-K1 (wild-type) cells incubated with 1% (v/v) DMSO (A) or 6 μM adhesamine (B). (C) and (D) show CHO 677 incubated with 1% (v/v) DMSO (A) or 6 μM adhesamine (B). (E) shows adhesion of CHO-K1 and its mutants when 6 μM of adhesamine was added to the culture media. Cells were seeded onto adhesamine-added or fibronectin-coated plastic wells. The concentrations of adhesamine and fibronectin were 6 μM and 5 μg/mL, respectively. Adhered cells were counted at 5 hours after seeding. Each point represents average±SD.

To further validate the interaction of adhesamine with heparan sulfate, CHO-K1 cell mutants deficient in glycosaminoglycan synthesis, including CHO 745, CHO 677, CHO 606 and CHO F17 were used. CHO 745 cells are unable to synthesize heparan sulfate and chondroitin sulfate, and CHO 677 cells exhibit reduced expression of heparan sulfate and an increased chondroitin sulfate[14,15]. Both of these cells lines were less responsive to adhesamine than parental CHO-K1 cells (FIG. 10E). These data indicate that the adhesamine-induced cell adhesion is a heparan sulfate proteoglycan-dependent process, and that the absence of heparan sulfate cannot be compensated for by increasing the level of expression of chondroitin sulfate.

CHO 606 cells, which lack GlcNAc N-deacetylase/N-sulfotransferase-1 activity, were also less responsive to adhesamine (FIG. 10E)[16]. In contrast, 2-O-sulfotransferase-deficient CHO F17 cells responded to adhesamine (FIG. 10E). These results suggest that N-sulfate groups in heparan sulfate are important elements for the interaction with adhesamine, whereas sulfate at C-2 of uronic acid residues are less crucial for binding.

Test Example 6

The cell adhesion mediated by integrins and cell surface heparan sulfate proteoglycans generates intercellular signals that stimulate a number of non-receptor kinases. Phosphorylation of focal adhesion kinase (FAK), the most prominent kinase activated by cell adhesion to extracellular matrix, was monitored in the presence of adhesamine. Time course analysis of FAK activation in Jurkat cells demonstrated FAK phosphorylation 5 hours after adhesamine stimulation (FIG. 11A). The activation was dose-dependent, and 5 μg/ml, of adhesamine was sufficient to phosphorylate FAK, whereas poly-L-lysine failed to do so at the same concentrations (FIG. 11B). The adhesamine-induced phosphorylation of FAK was reduced when cells were incubated with a competitive concentration of heparin (FIG. 11C). Addition of the RGD peptide, in contrast, had no detectable effects (FIG. 11C). Western blots performed in parallel showed no significant change in the total FAK levels in the cell lysates[18].

Figure 11:
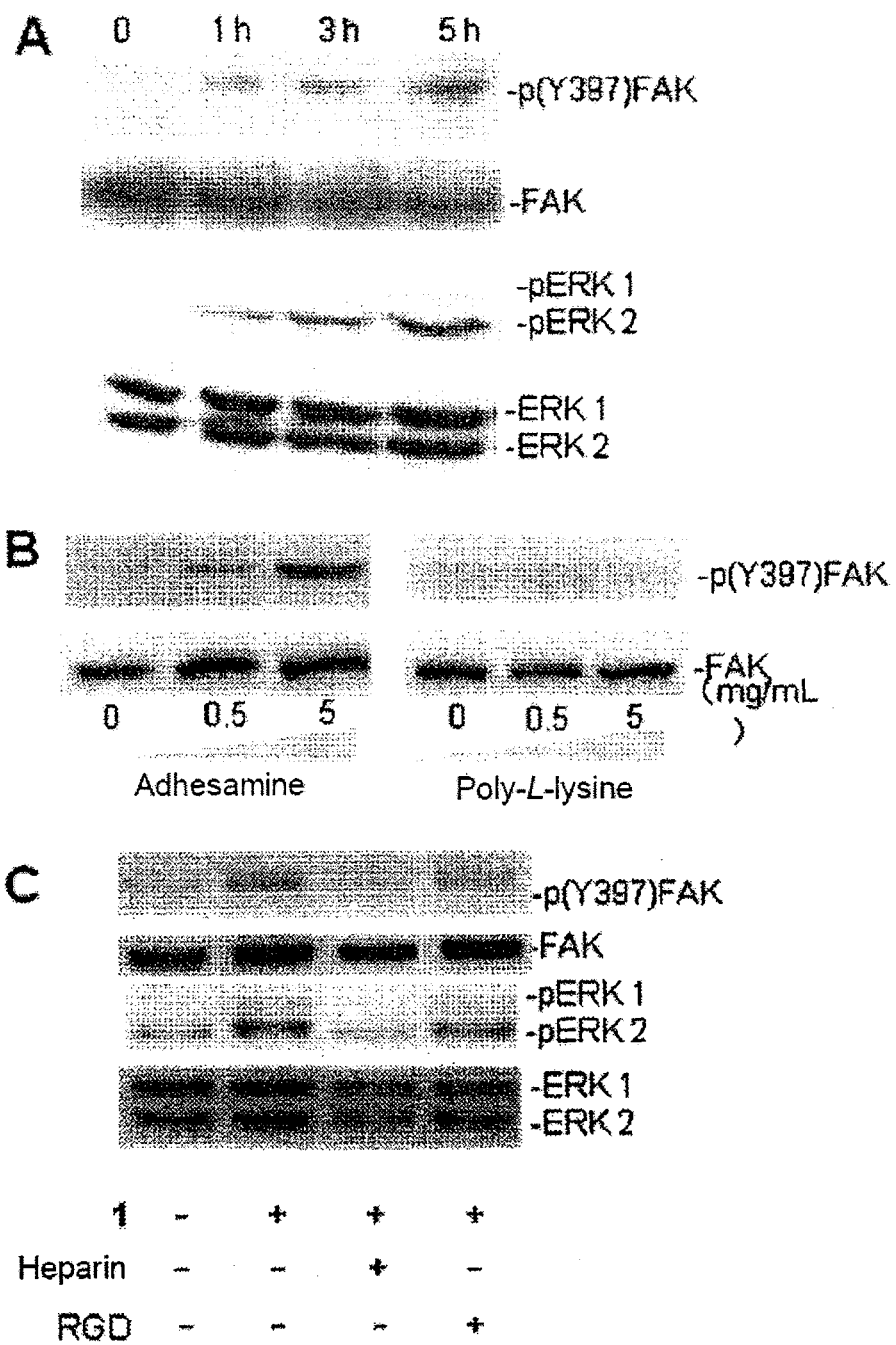
FIG. 11 shows FAK and ERK activation by adhesamine. (A) shows the time course of FAK and ERK activation upon adhesamine treatment. Jurkat cells were treated with adhesamine (6 μM) in a serum-poor culture medium (0.1% FBS) for the indicated periods of time. The treated cell lysates were Western blotted with antibodies against FAK phospho-tyrosine$^{397}$ (pFAK), FAK, ERK1/2 phospho-threonine$^{202}$/tyrosine$^{204}$ (pERK) or ERK. In (B), Jurkat cells were incubated for 5 hours with varied concentrations of adhesamine or poly-L-lysine. The cell lysates were Western blotted with antibodies against FAK phospho-tyrosine$^{397}$ or FAK. (C) shows effects of excess amounts of heparin or an RGD peptide (100 μg/mL). The concentration of adhesamine (1) was 6 μM.

Similar results were obtained with extracellular signal-regulated kinase (ERR), a down-stream kinase that is activated by FAK: ERK was phosphorylated 5 hours after incubation with adhesamine, and its activation was blocked by addition of excess amounts of heparin (FIG. 11). Activation of FAK and ERK plays important roles in cell motility, cell growth, cytoskeletal organization, and adhesion-dependent cell survival[19,20]. The phosphorylation of these two kinases may account for the cytoskeletal-organizing and growth-promoting activities of adhesamine.

Test Example 7

Figure 12:
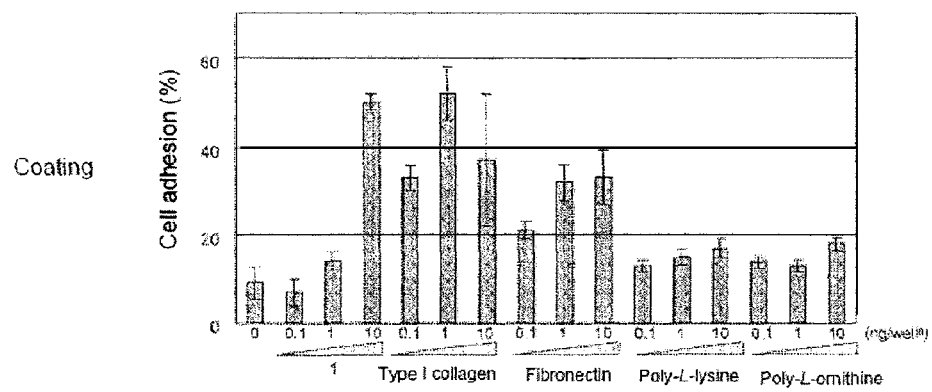
FIG. 12 shows cell adhesion-promoting activity of Compound 1 and coating materials. Data show the means±SD of three experiments. The surface area per well is 0.3 cm$^2$.
Figure 12:
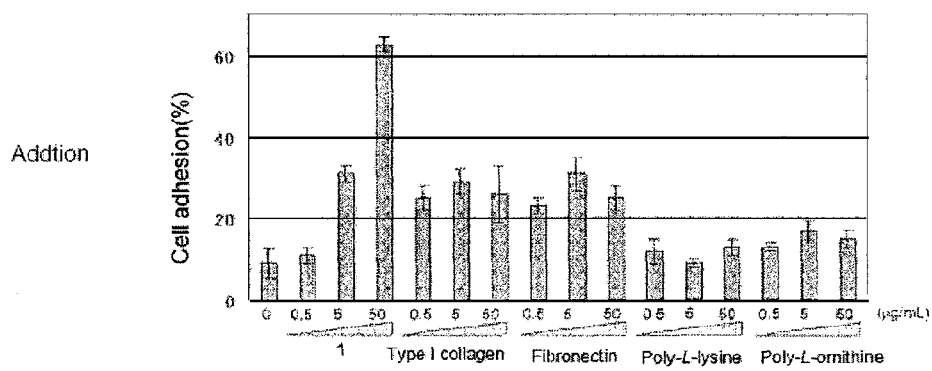

The effect of adhesamine on cell attachment was compared with effects of four commonly used plate-coating reagents: type I collagen, fibronectin, poly-L-lysine, and poly-L-ornithine. Addition of adhesamine to the medium caused significantly greater attachment than addition of the other coating reagents (FIG. 12). Similar activity was observed when adhesamine and the coating agents were applied. In this case, adhesamine at a concentration of 50 μg/well had a greater effect than fibronectin, poly-L-lysine, and poly-L-ornithine.

Test Example 8

Figure 13:
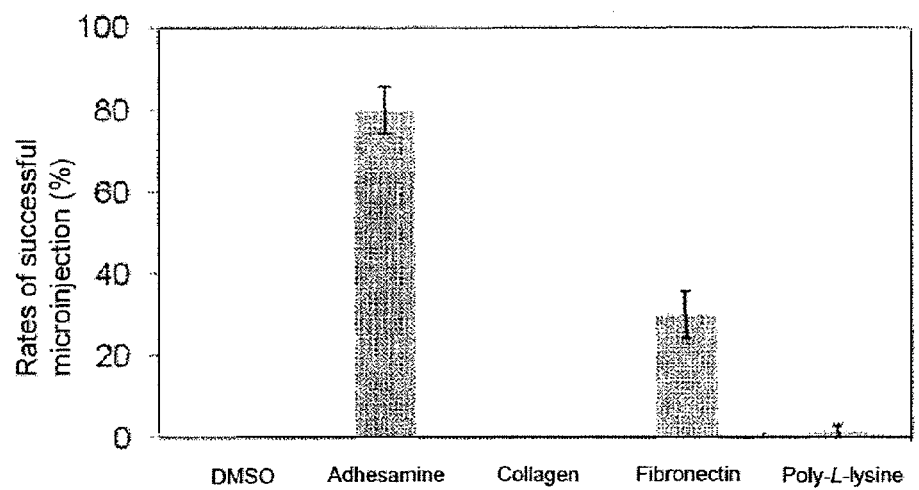
FIG. 13 shows a graph illustrating microinjection of a fluorescent dye (Alexa Fluor 594) into Jurkat cells in the presence of adhesamine (1). Adhesamine increases microinjection success rates more than type I collagen, poly-L-lysine hydrochloride, and fibronectin. The concentration of the reagents used was 5 μg/mL.

One possible application of adhesamine may be its use as a reagent that boosts microinjection, since tight attachment of cells to a plate is generally required for successful microinjection. To test this possibility, we examined whether adhesamine enables microinjection into Jurkat cells, an experiment that has been considered technically difficult due to the nonadherent characteristics of the lymphocytes. In fact, microinjection of a fluorescent dye, Alexa Fluor 594, into the cells was completely unsuccessful in the absence of adhesamine. Addition of type I collagen or poly-L-lysine to the culture exhibited almost no effects, and that of fibronectin improved the success rates up to 30% (FIG. 13). Addition of the same amounts of adhesamine, however, boosted the success rates as much as 80% (FIG. 13). Adhesamine may serve as a synthetic reagent that enables or aids microinjection into hard-to-inject cells.

REFERENCES

1. Hoshida, T., Nagahara, H., Cho, C., Tagawa, Y., Araike, T. (2007) Biomaterials, 28, 1093-1104
2. Huo, X., Xu, X. J., Chen, Y. W., Yang, H. W., and Piao, Z. X. (2004) World J Gastroenterol. 10, 1666-1668
3. Parsey, M. V., and Lewis, G. K. (1993) J Immunol 151, 1881-1893
4. Arroyo, A. G., Sanchez-Mateos, P., Campanero, M. R., Martin-Padura, I., Dejana, E., and Sanchez-Madrid, F. (1992) J Cell Biol 117, 659-670
5. Kinch, M. S., Strominger, J. L., and Doyle, C. (1993) J Immunol 151, 4552-4561
6. Schmidtke, M., Riabova, O., Dahse, H. M., Stelzner, A., and Makarov, V. (2002) Antiviral Res 55, 117-127
7. Bernfield, M., Gotte, M., Park, P. W., Reizes, O., Fitzgerald, M. L., Lincecum, J., and Zako, M. (1999) Annu Rev Biochem 68, 729-777
8. Oohira, A. K., Y., Tokita, Y., Sugiura, N., Sakurai, K., Suzuki, S., and Kimata, K. (2000) Archives of Biochemistry and Biophysics 378, 78-83
9. Cole, G. J. a. M., C. F. (1991) Neuron7, 729-777
10. Gupta, S., and Datta, K. (1991) Exp Cell Res 195, 386-394
11. Gallagher, J. T. (1989) Curr Opin Cell Biol 1, 1201-1218
12. Hernaiz, M. J., LeBrun, L. A., Wu, Y., Sen, J. W., Linhardt, R. J., and Heegaard, N. H. (2002) Eur J Biochem 269, 2860-2867
13. Gatti, G., Casu, B., Hamer, G. K., and Perlin, A. S. (1979) Macromolecules 12, 1001-1007
14. Esko, J. D., Stewart, T. E., and Taylor, W. H. (1985) Proc Natl Acad Sci USA 82, 3197-3201
15. Zhang, L., and Esko, J. D. (1995) J Biol Chem 270, 12557-12562
16. Bame, K. J., and Esko, J. D. (1989) J Biol Chem 264, 8059-8065
17. Bai, X., and Esko, J. D. (1996) J Biol Chem 271, 17711-17717
18. Maguire, J. E., Danahey, K. M., Burkly, L. C., and van Seventer, G. A. (1995) J Exp Med 182, 2079-2090
19. Gilmore, A. P., Burridge, K. (1996) Structure 4, 647-651
20. Zhao, J. H., Reiske, H., and Guan, J. L. (1998) J Cell Biol 143, 1997-2008

INDUSTRIAL APPLICABILITY

Due to its activity that enhances adhesion to the cell culture plate, adhesamine is applicable to cell adhesives, plate coating agents etc. in the field of cell biology.

The invention claimed is:
1. A dispirotripiperazine derivative represented by Formula I below or a salt thereof,

[Chem. 1]

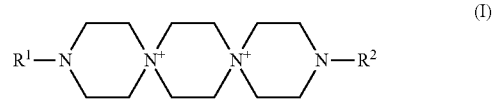

(I)

wherein $R^1$ and $R^2$ are the same or different, and each represent hydrogen, an alkyl group, an alkenyl group, an alkynyl group, a cycloalkyl group, a cycloalkylalkyl group, an aryl group, a heteroaryl group, an aryl-substituted alkyl group, a heteroaryl-substituted alkyl group (excluding the case where both $R^1$ and $R^2$ are hydrogen; at least one of $R^1$ and $R^2$ being bonded with a substance having integrin-binding activity, wherein the substance comprises Arg-Gly-Asp amino acid sequence; the alkyl group, the alkenyl group, the alkynyl group, and each alkyl moiety are optionally substituted with at least one atom or one group selected from halogen, hydroxyl (the hydroxy being optionally acylated, carbamated or etherified), cyano, nitro, amino, mono- or di-substituted amino, carbamoyl and sulfamoyl; the alkyl group, the alkenyl group, the alkynyl group, the cycloalkyl group, each alkyl moiety and each cycloalkyl moiety are optionally interrupted by —O—, —S—, —SO—, —SO$_2$—, —OSO$_2$—, —NH—, —CO—, —CH═CH—, —C≡C—, —CONH—, —NHCO—, —NHCOO—, —OCH$_2$CONH—, or —OCH$_2$CO—; and the aryl group, each aryl moiety, the heteroaryl group, each heteroaryl moiety, the cycloalkyl group and each cycloalkyl moiety are optionally substituted with at least one atom or one group selected from halogen, hydroxyl, formyl, alkyl, hydroxyalkyl, alkoxy, alkylthio, cyano, nitro, amino, mono- or di-substituted amino, carbamoyl, sulfamoyl, alkyl sulfonyl, alkyl sulfonylamino, alkyl carbonylamino, methylenedioxy, and aryl) or a group represented by Formula II below (excluding the case where both of $R^1$ and $R^2$ are a group represented by Formula II),

[Chem. 2]

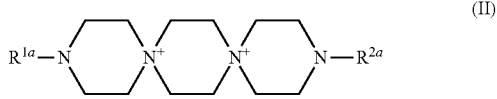

(II)

wherein $R^{1a}$ represents an alkylene group, an alkenylene group, an alkynylene group, a cycloalkylene group, a cycloalkylalkylene group, an arylene group, a heteroarylene group, an aryl-substituted alkylene group, or a heteroaryl-substituted alkylene group (the alkylene group, the alkenylene group, the alkynylene group, and each alkylene moiety being optionally substituted with at least one atom or one group selected from halogen, hydroxyl (the hydroxy being optionally acylated, carbamated or etherified), cyano, nitro, amino, mono- or di-substituted amino, carbamoyl and sulfamoyl; the alkylene group, the alkenylene group, the alkynylene group, the cycloalkylene group, each alkylene moiety and each cycloalkyl moiety are optionally interrupted by —O—, —S—, —SO—, —SO$_2$—, —OSO$_2$—, —NH—, —CO—, —CH=CH—, —C≡C—, —CONH—, —NHCO—, —NHCOO—, —OCH$_2$CONH—, or —OCH$_2$CO—; and the arylene group, each aryl moiety, the heteroarylene group, each heteroaryl moiety, the cycloalkylene group and each cycloalkyl moiety are optionally substituted with at least one atom or one group selected from halogen, hydroxyl, formyl, alkyl, hydroxyalkyl, alkoxy, alkylthio, cyano, nitro, amino, mono- or di-substituted amino, carbamoyl, sulfamoyl, alkyl sulfonyl, alkyl sulfonylamino, alkyl carbonylamino, methylenedioxy, and aryl); and $R^{2a}$ has the same definition as those of $R^1$ and $R^2$.

2. A dispirotripiperazine derivative represented by Formula Ia below or a salt thereof,

[Chem. 11]

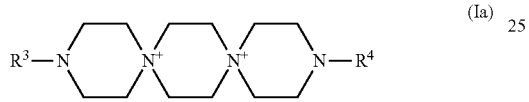

(Ia)

wherein $R^3$ represents a monocyclic aryl group or a monocyclic heteroaryl group ($R^3$ being optionally derivatized with dansylhydrazine or bonded with a substance having integrin-binding activity or a Arg-Gly-Asp peptide; and the aryl group and the heteroaryl group are optionally substituted with at least one atom or one group selected from halogen, hydroxyl formyl, alkyl, hydroxyalkyl, alkoxy, alkylthio, cyano, nitro, amino, mono- or di-substituted amino, carbamoyl, sulfamoyl, alkyl sulfonyl, alkyl sulfonylamino, alkyl carbonylamino, methylenedioxy, and aryl); and $R^4$ represents a group represented by Formula IIa below,

[Chem. 12]

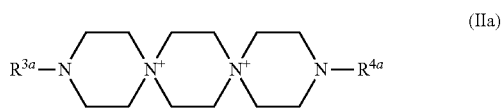

(IIa)

wherein $R^{3a}$ represents a monocyclic arylene group or monocyclic heteroarylene group, (the arylene group and heteroarylene group being optionally substituted with at least one atom or one group selected from the group consisting of halogen, hydroxyl, formyl, alkyl, hydroxyalkyl, alkoxy, alkylthio, cyano, nitro, amino, mono- or di-substituted amino, carbamoyl, sulfamoyl, alkyl sulfonyl, alkyl sulfonylamino, alkyl carbonylamino, methylenedioxy, and aryl), and $R^{4a}$ has the same definition as that of $R^3$.

3. A dispirotripiperazine derivative or a salt thereof selected from the groups below:

[Chem. 13]

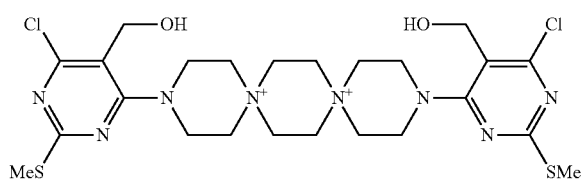

(b)

[Chem. 14]

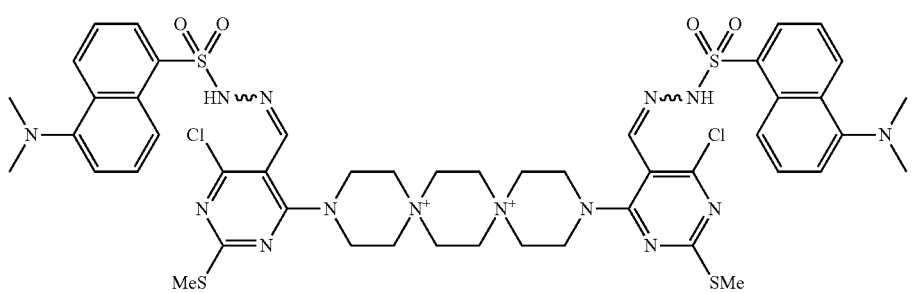

(c)

[Chem. 15]

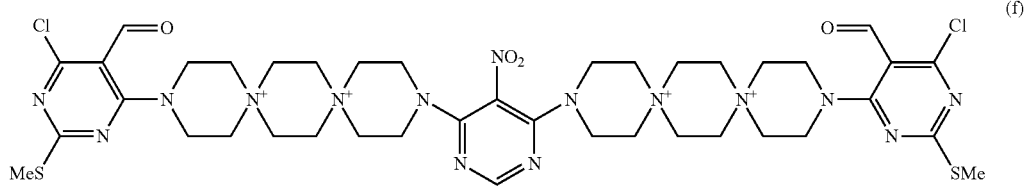

(f)

-continued

[Chem. 16]

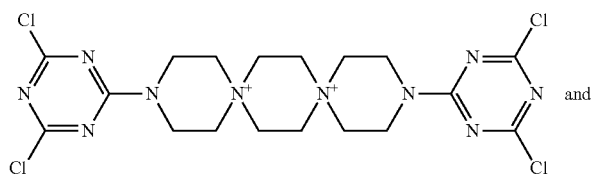

(g)

and

[Chem. 17]

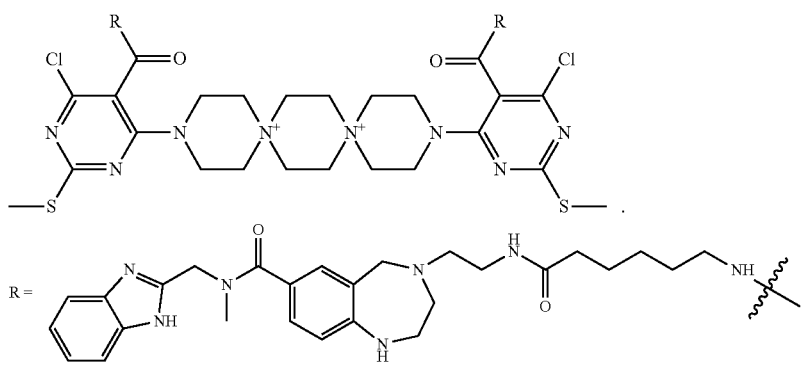

(h)

4. A method for promoting cell adhesion to a support, comprising either adding the dispirotripiperazine derivative or a salt thereof according to claim 1 to a culture medium, or applying the dispirotripiperazine derivative or a salt thereof according to claim 1 to a support.

5. The method according to claim 4, wherein the support is a cell culture vessel.

6. The method according to claim 4, wherein the cell is a nonadherent cell.

7. A method for promoting cell adhesion to a support, comprising either adding the dispirotripiperazine derivative or a salt thereof according to claim 2 to a culture medium, or applying the dispirotripiperazine derivative or a salt thereof according to claim 2 to a support.

8. The method according to claim 7, wherein the support is a cell culture vessel.

9. The method according to claim 7, wherein the cell is a nonadherent cell.

10. A method for promoting cell adhesion to a support, comprising either adding the dispirotripiperazine derivative or a salt thereof according to claim 3 to a culture medium, or applying the dispirotripiperazine derivative or a salt thereof according to claim 3 to a support.

11. The method according to claim 10, wherein the support is a cell culture vessel.

12. The method according to claim 10, wherein the cell is a nonadherent cell.

* * * * *